(12) United States Patent
Shaver et al.

(10) Patent No.: US 9,695,101 B2
(45) Date of Patent: Jul. 4, 2017

(54) PROCESSES FOR PRODUCING ACETIC ACID WITH DECANTER CONTROL

(71) Applicant: Celanese International Corporation, Irving, TX (US)

(72) Inventors: Ronald D. Shaver, Houston, TX (US); Yaw-Hwa Liu, Missouri City, TX (US); Mark O. Scates, Houston, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 0 days.

(21) Appl. No.: 14/873,614

(22) Filed: Oct. 2, 2015

(65) Prior Publication Data

US 2016/0137581 A1 May 19, 2016

Related U.S. Application Data

(60) Provisional application No. 62/079,918, filed on Nov. 14, 2014.

(51) Int. Cl.
  *C07C 51/10* (2006.01)
  *C07C 51/44* (2006.01)
  *C07C 51/12* (2006.01)

(52) U.S. Cl.
  CPC .......... *C07C 51/445* (2013.01); *C07C 51/12* (2013.01); *C07C 51/44* (2013.01)

(58) Field of Classification Search
  CPC ....... C07C 51/445; C07C 51/12; C07C 53/08; C07C 51/44; A01B 12/006
  See application file for complete search history.

(56) References Cited

U.S. PATENT DOCUMENTS 3,791,935 A  2/1974 Eubanks et al.
4,008,131 A  2/1977 Price
(Continued)

FOREIGN PATENT DOCUMENTS

WO  WO2012/046593  *  4/2012
WO  2014/115826 A1  7/2014

OTHER PUBLICATIONS

Haynes, A. (2010). "Catalytic Methanol Carbonylation," *Advances in Catalysis* 53:1-45.
(Continued)

*Primary Examiner* — Yevegeny Valenrod
*Assistant Examiner* — Blaine G Doletski
(74) *Attorney, Agent, or Firm* — Kilpatrick Townsend & Stockton LLP

(57) ABSTRACT

A process for producing acetic acid comprising the steps of carbonylating methanol in a reaction medium to form a crude acetic acid product; conveying the crude acetic acid product to a flash vessel at a flash flow rate; flashing the crude acetic acid product to form a first vapor stream comprising acetic acid and a liquid residue stream comprising metal catalyst and halide salt; separating the flashed vapor stream to form a second vapor stream comprising methyl iodide a sidedraw comprising purified acetic acid and water, and a liquid residue stream. The process further comprises the steps of condensing at least a portion of the second vapor stream to form at least one liquid phase and refluxing to the light ends column at least a portion of the at least one liquid phase at a reflux rate. The reflux rate is adjusted based on changes in the flash flow rate.

23 Claims, 2 Drawing Sheets

(56) References Cited

U.S. PATENT DOCUMENTS

| | | | |
|---|---|---|---|
| 4,039,395 | A | 8/1977 | Eby |
| 5,001,259 | A | 3/1991 | Smith et al. |
| 5,352,415 | A | 10/1994 | Ochiai |
| 5,416,237 | A | 5/1995 | Aubigne et al. |
| 5,625,095 | A | 4/1997 | Miura et al. |
| 5,723,660 | A | 3/1998 | Morimoto et al. |
| 6,143,930 | A | 11/2000 | Singh et al. |
| 6,458,996 | B1 | 10/2002 | Muskett |
| 6,552,221 | B1 | 4/2003 | Hallinan et al. |
| 6,657,078 | B2 | 12/2003 | Scates et al. |
| 7,052,657 | B2 | 5/2006 | Nakajima et al. |
| 7,476,761 | B2 | 1/2009 | Kojima |
| 7,683,212 | B2 | 3/2010 | Kojima et al. |
| 7,855,306 | B2 | 12/2010 | Zinobile et al. |
| 7,884,241 | B2 | 2/2011 | Miura et al. |
| 8,940,932 | B2 * | 1/2015 | Shimizu .................. C07C 51/12 562/519 |
| 8,957,248 | B2 | 2/2015 | Miura et al. |
| 9,006,483 | B2 | 4/2015 | Shimizu et al. |
| 9,073,843 | B2 | 7/2015 | Shimizu et al. |
| 9,115,071 | B2 | 8/2015 | Shimizu et al. |
| 2006/0247466 | A1 | 11/2006 | Zinobile et al. |
| 2011/0288333 | A1* | 11/2011 | Shaver .................... C07C 51/44 562/608 |
| 2013/0264186 | A1 | 10/2013 | Shimizu et al. |
| 2013/0281735 | A1 | 10/2013 | Shimizu et al. |

OTHER PUBLICATIONS

Haynes, A. (2006, e-pub. May 25, 2006). "Acetic Acid Synthesis by Catalytic Carbonylation of Methanol," in Topics in Organometallic Chemistry, Catalytic Carbonylation Reactions, Springer-Verlag, Berlin, Heidelberg, 18:179-205.

Jones, J.H. (2000). "The Cativa™ Process for the Manufacture of Acetic Acid," Platinum Metals Review 44(3):94-105.

Zhu, Y. et al. (Apr. 2009). "Techno-economic Analysis for the Thermochemical Conversion of Lignocellulosic Biomass to Ethanol via Acetic Acid Synthesis," prepared for U.S. Department of Energy, PNNL-18483, Pacific Northwest National Laboratory, Richland, WA, 79 pages.

International Search Report and Written Opinion received in the corresponding PCT Application No. PCT/US2015/053661, dated Jan. 18, 2016.

Declaration by James B. Riggs, Appendix A from IPR2017-00163, dated Oct. 30, 2016.

Balchen, Jens, G., et al., "Process Control, Structure and Applications", *Van Nostrand Reinhold*, 1988.

Baasel, William D., "Chemical Engineering Plant Design", *Van Nostrand Reinhold*, 1990.

English Translation of International Search Report for International patent application No. PCT/JP2011/072059, dated Jan. 21, 2012.

Extended European Search Report for European Patent Application No. 11830526.7, dated Sep. 11, 2014.

Notice of Allowance received in U.S. Appl. No. 13/825,266, dated Nov. 5, 2014.

Kister, Henry Z., *Distillation Operation*, McGraw Hill, 1990.

Nunes, G.C., "A Practical Strategy for Controlling Flow Oscillations in Surge Tanks" *Latin American Applied Research*, 37:195-200, 2007.

Response to the Search Report for European Patent Application No. 11830526.7, dated and filed on Mar. 25, 2015.

Riggs, James B., *Chemical Process Control*, $2^{nd}$ Edition-Chapter 1, Ferret Publishing, 2001.

Sinnot, R.K., "An Introduction to Chemical Engineering Design", *Chemical Engineering*, vol., 6, 1983.

Torrence, P., "Chapter 2.1.2 Carbonylations" *Applied Homogeneous Catalysis with Organometallic Compounds*, Ed. 2, pp. 104-136.

Calculation of Example 1 of U.S. Pat. No. 5,416,237, included in the IPR dated Oct. 31, 2016.

Calculation of Example 2 of U.S. Pat. No. 5,416,237, included in the IPR dated Oct. 31, 2016.

* cited by examiner

PROCESSES FOR PRODUCING ACETIC ACID WITH DECANTER CONTROL

CROSS-REFERENCES TO RELATED APPLICATION

This patent application claims priority to U.S. Provisional Patent Application No. 62/079,918, filed Nov. 14, 2014, the disclosure of this application is incorporated herein by reference in its entirety.

FIELD OF THE INVENTION

This invention relates to processes for producing acetic acid and, in particular, to improved processes for producing acetic acid that exhibit effective light ends column control and/or decanter liquid level control.

BACKGROUND OF THE INVENTION

A widely used and successful commercial process for synthesizing acetic acid involves the catalyzed carbonylation of methanol, e.g., a methanol (feed) composition, with carbon monoxide. The catalyst may contain rhodium and/or iridium and a halogen promoter, typically methyl iodide. The reaction is conducted by continuously bubbling carbon monoxide through a liquid reaction medium in which the catalyst is dissolved. The reaction medium comprises acetic acid, methyl acetate, water, methyl iodide and the catalyst. The methanol and the carbon monoxide come into contact in the reaction medium and react with one another to form crude acetic acid. Conventional commercial processes for the carbonylation of methanol include those described in U.S. Pat. Nos. 3,769,329, 5,001,259, 5,026,908, and 5,144,068, the entireties of which are incorporated herein by reference. Another conventional methanol carbonylation process includes the Cativa™ process, which is discussed in Jones, J. H. (2002), "*The Cativa™ Process for the Manufacture of Acetic Acid*," Platinum Metals Review, 44 (3): 94-105, the entirety of which is incorporated herein by reference.

Typically, crude acetic acid is separated using a separation train having inter alia a carbonylation reactor, a flash vessel, a light ends column, and a decanter. U.S. Pat. No. 7,855,306, the entirety of which is incorporated herein by reference, discloses a process, e.g., a process comprising a separation zone, for reduction and/or removal of PRCs from a carbonylation product by (a) separating the carbonylation product to provide a vapor overhead stream; (b) distilling the vapor overhead stream to yield a low boiling overhead vapor stream; (c) condensing and separating the low boiling overhead vapor stream to form a condensed light liquid phase; (d) distilling the condensed light liquid phase in a single distillation column to form a second vapor phase stream enriched with PRC's; and (e) condensing and extracting the second vapor phase stream with water to obtain an aqueous acetaldehyde stream comprising PRCs.

U.S. Pat. No. 8,940,932 discloses a process for stably producing high-purity acetic acid while efficiently removing acetaldehyde. The process for producing acetic acid comprises a reaction step for allowing methanol to react with carbon monoxide in the presence of a metal catalyst, a halide salt, and methyl iodide; a step for continuously feeding a flash vessel with the reaction mixture and separating a lower boiling point component containing acetic acid and methyl iodide and a higher boiling point component containing the metal catalyst and the halide salt; a step for feeding a distillation column with the lower boiling point component, and separating a lower boiling point component containing methyl iodide and acetaldehyde and a stream containing acetic acid to collect acetic acid; a condensation step for condensing and temporarily holding the lower boiling point component in a decanter and discharging the lower boiling point component from the decanter; and a step for separating the lower boiling point component discharged from the decanter into acetaldehyde and a liquid residue and recycling the liquid residue to the reaction system. In the condensation step, the amount of the lower boiling point component to be held is controlled based on a fluctuating flow rate of the lower boiling point component to be fed to the decanter.

While the above-described processes have provided some processes for separating crude acetic acid, specifically for maintaining the liquid level in a decanter/condenser, these processes establish control by measuring the light ends overhead stream and then varying the recycle streams to the reaction zone, which may create problems with respect to the overall water balance in the reaction system and, in some cases may provide for insufficient control. These methods may also require the use of additional process components or the modification of process components, e.g., decanters with buffering capability. Thus, the need exists for improved processes for maintaining consistent light ends and decanter operations, which provide for: 1) a more consistent purified product composition e.g., a more consistent light ends column as a sidedraw composition, and 2) more precise liquid level control without disturbing the water balance in the reaction system or requiring additional process components or process modifications.

SUMMARY OF THE INVENTION

The present invention relates to processes for producing acetic acid. In some embodiments, the processes comprise the step of carbonylating at least one reactant selected from the group consisting of methanol, dimethyl ether, methyl acetate, and mixtures thereof, in a reaction medium comprising a metal catalyst, methyl iodide, a halide salt, and optionally a finite amount water, to form a crude acetic acid product. The processes may further comprise the step of conveying the crude acetic acid product to a flash vessel at a flash flow rate. The flow of the crude acetic acid to the flash vessel (the "flash flow") is preferably liquid in state. The flash flow rate may be measured by conventional methods, e.g., flow meters. The crude acetic acid product is flashed, with or without heat, to form a first vapor stream and a first liquid residue stream. The first vapor stream comprises acetic acid and methyl iodide. The first liquid residue stream comprises metal catalyst and halide salt and may be recycled to the reactor. The flashed first vapor stream is separated in a light ends column to form a second vapor stream, a sidedraw, and a second liquid residue stream. The second vapor stream comprises methyl iodide and optionally acetaldehyde. The sidedraw comprises purified acetic acid product and optionally water. The second residue stream comprises acetic acid, water, and catalyst and may be recycled to the reactor. At least a portion of the second vapor stream is condensed in a decanter to form at least one liquid phase. The at least one liquid phase, in some embodiments, comprises a light phase. In some embodiments, the at least one liquid phase comprises a heavy phase. In some embodiments, the at least one liquid phase comprises both a light liquid phase and a heavy phase. A liquid level is established in the decanter by the condensation of the second vapor stream. The liquid level is generally the level to which the liquid phases rise. The liquid level is maintained so as to avoid upsets or overflows of the decanter. At least a portion of the at least one liquid phase is refluxed to the light ends column, thus establishing a reflux loop. In some cases, the light phase is refluxed to establish the reflux loop. In some cases, the heavy phase is refluxed to establish the reflux loop. It is also contemplated that both the heavy phase and the light phase are refluxed to establish the reflux loop(s). The reflux loop has a reflux rate, which is the flow rate at which the at least one liquid phase is returned to the light ends column. The reflux rate generally may be measured by conventional methods, e.g., flow meters. The reflux rate is adjusted based on changes in the flash flow rate. For example, as flash flow rate increases, reflux rate may be adjusted for the greater amount of flow entering the flash vessel. The greater amount of flow may also have a subsequent effect on flow into the light ends column and decanter liquid level. In some cases, the processes may comprise the step of controlling the liquid level in the decanter based on at least one of flash flow rate and reflux rate, e.g., based on the flash flow rate, based on the reflux rate, or based on both the flash flow rate and the reflux rate. The variances in sidedraw concentrations are improved. For example, the water concentration in the sidedraw may vary by +/−0.3%, under steady state operation, e.g., +/−0.2% or +/−0.1%, and/or the water concentration in the sidedraw may range from 1.1 wt. % to 3 wt. %, e.g., from 1.3 wt. % to 2.7 wt. % or from 1.5 wt. % to 2.5 wt. %.

The invention also relates to a process for producing acetic acid. The process comprises the step of carbonylating methanol in a reaction medium to form a crude acetic acid product. The reaction medium comprises a metal catalyst, methyl iodide, a halide salt, and optionally water. The process further comprises the step of flashing the crude acetic acid product, with or without heat, to form a first vapor stream comprising acetic acid and optionally methyl iodide and a first liquid residue stream comprising metal catalyst and halide salt; separating, in a light ends column, the flashed vapor stream to form a second vapor stream comprising methyl iodide and optionally acetaldehyde, a sidedraw comprising purified acetic acid product, and a second liquid residue stream; and condensing, in a decanter, at least a portion of the second vapor stream to form at least one liquid phase, e.g., a heavy phase and/or a light phase. The process further comprises the steps of refluxing to the light ends column at least a portion of the at least one liquid phase at a reflux rate. The process further comprises the step of controlling a liquid level in the decanter via the reflux rate. The controlling may comprise the step of measuring the liquid level in the decanter and adjusting the reflux rate in response to the liquid level and increasing the reflux rate if the liquid level increases or decreasing the reflux rate if the liquid level decreases. Preferably, the liquid level in the decanter is substantially constant under steady state operation. The carbonylation may occur in a reactor and water content in the reactor may be maintained at a substantially constant level under steady state operation. The process may further comprise the step of dehydrating, in a drying column, the sidedraw to form a dehydrated acetic acid product comprising acetic acid and a minor amount of water and the water concentration in the sidedraw fed to the drying column is substantially constant under steady state operation, e.g., the water concentration varies by +/−0.3%, for example ranging from 1.1 wt % to 3 wt %, based on the total weight of the sidedraw. In one embodiment, the heavy phase is formed, the specific gravity of the heavy phase is substantially constant under steady state operation, e.g., the specific gravity of the heavy phase varies by +/−0.05, for example ranging from 1.5 to 1.8. The process may further comprise the step of directing the at least one liquid phase to a permanganate reducing compound removal system at a PRS feed rate and the PRS feed rate is substantially constant, under steady state operation. In one embodiment, the at least one liquid phase comprises a light phase and the light phase is refluxed to the light ends column. The specific gravity of the light phase may be substantially constant, under steady state operation, e.g., the specific gravity of the light phase varies by +/−0.05, for example ranging from 0.9 to 1.2, under steady state operation.

BRIEF DESCRIPTION OF THE DRAWING

The present invention will be better understood in view of the appended non-limiting figure, wherein.

DETAILED DESCRIPTION OF THE INVENTION

Figure 1:
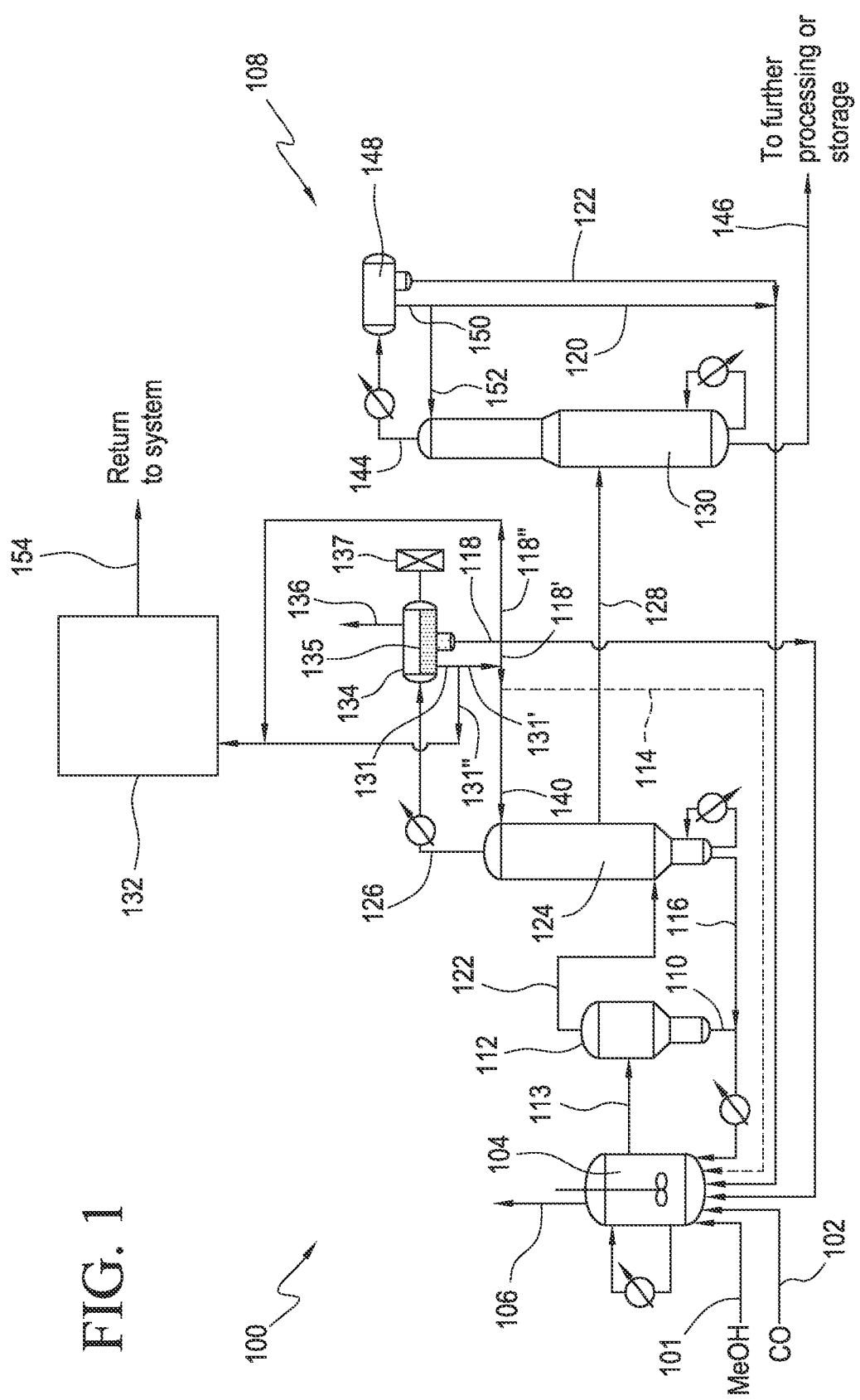
FIG. 1 shows a schematic of an acetic acid production process in accordance with the present invention.

At the outset, it should be noted that in the development of any such actual embodiment, numerous implementation-specific decisions must be made to achieve the developer's specific goals, such as compliance with system related and business related constraints, which will vary from one implementation to another. In addition, the processes disclosed herein can also comprise components other than those cited or specifically referred to, as is apparent to one having average or reasonable skill in the art.

In the summary and this detailed description, each numerical value should be read once as modified by the term "about" (unless already expressly so modified), and then read again as not so modified unless otherwise indicated in context. Also, in the summary and this detailed description, it should be understood that a concentration range listed or described as being useful, suitable, or the like, is intended that any and every concentration within the range, including the end points, is to be considered as having been stated. For example, a range "from 1 to 10" is to be read as indicating each and every possible number along the continuum between about 1 and about 10. Thus, even if specific data points within the range, or even no data points within the range, are explicitly identified or refer to only a few specific data points, it is to be understood that inventors appreciate and understand that any and all data points within the range are to be considered to have been specified, and that inventors possessed knowledge of the entire range and all points within the range.

Throughout the entire specification, including the claims, the following terms have the indicated meanings unless otherwise specified.

As used in the specification and claims, "near" is inclusive of "at." The term "and/or" refers to both the inclusive "and" case and the exclusive "or" case, and is used herein for brevity. For example, a mixture comprising acetic acid and/or methyl acetate may comprise acetic acid alone, methyl acetate alone, or both acetic acid and methyl acetate.

All percentages are expressed as weight percent (wt. %), based on the total weight of the particular stream or composition present, unless otherwise noted. Room temperature is 25° C. and atmospheric pressure is 101.325 kPa unless otherwise noted.

For purposes herein:
acetic acid may be abbreviated as "AcOH";
acetaldehyde may be abbreviated as "AcH";
methyl acetate may be abbreviated "MeAc";
methanol may be abbreviated "MeOH";
methyl iodide may be abbreviated as "MeI";
hydrogen iodide may be abbreviated as "HI";
carbon monoxide may be abbreviated "CO"; and
dimethyl ether may be abbreviated "DME".

HI refers to either molecular hydrogen iodide or dissociated hydriodic acid when at least partially ionized in a polar medium, typically a medium comprising at least some water. Unless otherwise specified, the two are referred to interchangeably. Unless otherwise specified, HI concentration is determined via acid-base titration using a potentiometric end point. In particular, HI concentration is determined via titration with a standard lithium acetate solution to a potentiometric end point. It is to be understood that for purposes herein, the concentration of HI is not determined by subtracting a concentration of iodide assumed to be associated with a measurement of corrosion metals or other non H+ cations from the total ionic iodide present in a sample.

It is to be understood that HI concentration does not refer to iodide ion concentration. HI concentration specifically refers to HI concentration as determined via potentiometric titration.

This subtraction method is an unreliable and imprecise method to determine relatively lower HI concentrations, e.g., less than about 5 weight percent) due to the fact that it assumes all non-H+ cations (such as cations of Fe, Ni, Cr, Mo) are associated with iodide anion exclusively. In reality, a significant portion of the metal cations in this process can be associated with acetate anion. Additionally, many of these metal cations have multiple valence states, which adds even more unreliability to the assumption on the amount of iodide anion which could be associated with these metals. Ultimately, this method gives rise to an unreliable determination of the actual HI concentration, especially in view of the ability to perform a simple titration directly representative of the HI concentration.

For purposes herein, an "overhead" or "distillate" of a distillation column refers to at least one of the lower boiling condensable fractions which exits at or near the top, (e.g., proximate to the top), of the distillation column, and/or the condensed form of that stream or composition. Obviously, all fractions are ultimately condensable, yet for purposes herein, a condensable fraction is condensable under the conditions present in the process as readily understood by one of skill in the art. Examples of noncondensable fractions may include nitrogen, hydrogen, and the like. Likewise, an overhead stream may be taken just below the upper most exit of a distillation column, for example, wherein the lowest boiling fraction is a non-condensable stream or represents a de-minimis stream, as would be readily understood by one of reasonable skill in the art.

The "bottoms" or "residuum" of a distillation column refers to one or more of the highest boiling fractions which exit at or near the bottom of the distillation column, also referred to herein as flowing from the bottom sump of the column. It is to be understood that a residuum may be taken from just above the very bottom exit of a distillation column, for example, wherein the very bottom fraction produced by the column is a salt, an unusable tar, a solid waste product, or a de-minimis stream as would be readily understood by one of reasonable skill in the art.

For purposes herein, distillation columns comprise a distillation zone and a bottom sump zone. The distillation zone includes everything above the bottom sump zone, e.g., between the bottom sump zone and the top of the column. For purposes herein, the bottom sump zone refers to the lower portion of the distillation column in which a liquid reservoir of the higher boiling components is present (e.g., the bottom of a distillation column) from which the bottom or residuum stream flows upon exiting the column. The bottom sump zone may include reboilers, control equipment, and the like.

It is to be understood that the term "passages", "flow paths", "flow conduits", and the like in relation to internal components of a distillation column are used interchangeably to refer to holes, tubes, channels, slits, drains, and the like, which are disposed through and/or which provide a path for liquid and/or vapor to move from one side of the internal component to the other side of the internal component. Examples of passages disposed through a structure such as a liquid distributor of a distillation column include drain holes, drain tubes, drain slits, and the like, which allow a liquid to flow through the structure from one side to another.

Average residence time is defined as the sum total of all liquid volume hold-up for a given phase within a distillation zone divided by the average flow rate of that phase through the distillation zone. The hold-up volume for a given phase can include liquid volume contained in the various internal components of the column including collectors, distributors and the like, as well as liquid contained on trays, within downcomers, and/or within structured or random packed bed sections.

Typical acetic acid reaction and separation processes utilize a separation train having inter alia a carbonylation reactor, a flash vessel, a light ends column, and a decanter.

The importance of maintaining a consistent liquid level in the decanter has been documented and some separation schemes have been developed in attempts to achieve this goal. For example, one conventional separation scheme utilizes a condensation (decanting) step in which a light ends overhead is condensed and a portion thereof is recycled to the reaction zone. In this case, the liquid level in the decanter is maintained by adjusting the amount of condensed light ends overhead that is recycled to the reaction zone. Unfortunately, the variances in the amount of condensed light ends that are recycled to the reaction system may create disturbances in the water balance in the reaction system and also may result in more fluctuations in the drying column feed. Also, in this separation scheme, the portion of the light ends overhead that is not recycled is directed to an aldehyde separation process. Because the recycled portion or portions vary during operation, the portion that is directed to the aldehyde separation process likewise varies. Thus, flow of light ends overhead to the aldehyde separation process may be highly inconsistent, which is detrimental to separation efficiency, e.g., aldehyde separation efficiency. In summary, in attempting to control liquid level in the decanter, this separation scheme creates problems with the water balance in the reaction system and as well as an inconsistent flow to the aldehyde separation process.

In addition to the inconsistencies mentioned above, the variances in the amount of condensed light ends that are recycled to the reaction system may create significant inconsistencies in light ends column operation. Because of the operation variances, the overall operation of the light ends column will be negatively affected. As a result, the composition of the light ends sidedraw will be inconsistent. For example, water content in the sidedraw will vary significantly, e.g., more than +/−2% or more than +/−1%, meaning that for a target of 3%, the composition could vary from 1% to 5% or from 2% to 4%. The inconsistencies in the sidedraw create additional problems in the downstream separation zone, e.g., in a drying column.

Another separation scheme utilizes a decanter having a buffering function, e.g., the decanter has enough capacity to ease the feed fluctuations into and out of the decanter. In this separation scheme, the decanter must often store a significant portion of the light ends overhead. The use of this type of decanter involves additional expense and its process control capabilities leave much room for improvement. In addition, the use of the buffering decanter typically retains a significant amount of methyl iodide, thus preventing the use thereof.

It has now been surprisingly and unexpectedly found that the flow, e.g., the liquid flow, of the crude acetic acid product from the reactor to the flash vessel can be effectively employed to control both light ends column and decanter operations. Beneficially, by utilizing the crude product flow to the flash vessel (and optionally the reflux flows from the decanter to the light ends column) a more efficient control scheme is established. For example, when using the disclosed control schemes, responses may be made as soon as the changes, e.g., changes in the flash flow rate, are noticed and in anticipation of the inevitable impact to the column, which avoids a disturbance. In contrast, with many conventional control schemes, e.g., control based on light ends overhead, the control is feedback control and no action is taken until the disturbance has already passed through the column and impacted the decanter. In some cases, the resultant control scheme is a feed forward control scheme based on the flash flow rate. As a result, light ends column operation and the composition exiting as a sidedraw are, advantageously, significantly more consistent. For example, with regard to water content in the sidedraw, the water concentration in the sidedraw may vary by +/−0.3%, under steady state operation, e.g., +/−0.2%, or +/−0.1%.

As noted above, it has also been discovered that the reflux to the light ends column of at least one of the liquid phases formed in the decanter can be used to effectively control the liquid level in the decanter (and light ends column operation). Liquid phases, e.g., the heavy phase and/or the light phase, are typically formed in the decanter as the light ends overhead is condensed. In most separation schemes, a portion of these liquid phases is returned to the light ends column, thus establishing a reflux loop. Although the use of a reflux loop is known, its potential for use in a process control scheme has not been considered. It has now been discovered that the rate at which the liquid phase(s) are returned to the light ends column, e.g., the reflux rate, may be advantageously used to control the liquid level in the decanter (and light ends column operation). By controlling the liquid level in this manner, as opposed to varying the liquid phase(s) that are recycled to the reactor, the deleterious effect on the water balance in the reaction system is minimized or eliminated. And, even in cases where the recycle streams may be varied, these recycle streams would be varied significantly less because the adjustments to the reflux rate will already be contributing significantly to the control scheme. Thus, while there may be changes to the water balance, such changes would be minimized.

Also, because the reflux loop already exists, no additional components need to be added to the process, e.g., a decanter with buffering capability, nor do other process modifications need to be made.

The present invention relates to processes for producing acetic acid. In some embodiments, the processes comprise the step of carbonylating at least one reactant selected from the group consisting of methanol, dimethyl ether, methyl acetate, and mixtures thereof, in a reaction medium comprising a metal catalyst, methyl iodide, a halide salt, and optionally a finite amount water, to form a crude acetic acid product. The processes may further comprise the step of conveying the crude acetic acid product to a flash vessel at a flash flow rate. The flow of the crude acetic acid to the flash vessel (the "flash flow") is preferably liquid in state. The flash flow rate may be measured by conventional methods, e.g., flow meters. The crude acetic acid product is flashed, with or without heat, to form a first vapor stream and a first liquid residue stream. The first vapor stream comprises acetic acid and methyl iodide. The first liquid residue stream comprises metal catalyst and halide salt and may be recycled to the reactor. The flashed first vapor stream is separated in a light ends column to form a second vapor stream, a sidedraw, and a second liquid residue stream. The second vapor stream comprises methyl iodide and optionally acetaldehyde. The sidedraw comprises purified acetic acid product and optionally water. The second residue stream comprises acetic acid, water, and catalyst and may be recycled to the reactor. At least a portion of the second vapor stream is condensed in a decanter to form at least one liquid phase. The at least one liquid phase, in some embodiments, comprises a light phase. In some embodiments, the at least one liquid phase comprises a heavy phase. In some embodiments, the at least one liquid phase comprises both a light liquid phase and a heavy phase. A liquid level is established in the decanter by the condensation of the second vapor stream. The liquid level is generally the level to which the liquid phases rise. The liquid level is maintained so as to avoid upsets or overflows of the decanter. At least a portion of the at least one liquid phase is refluxed to the light ends column, thus establishing a reflux loop. In some cases, the light phase is refluxed to establish the reflux loop. In some cases, the heavy phase is refluxed to establish the reflux loop. It is also contemplated that both the heavy phase and the light phase are refluxed to establish the reflux loop(s). The reflux loop has a reflux rate, which is the flow rate at which the at least one liquid phase is returned to the light ends column. The reflux rate generally may be measured by conventional methods, e.g., flow meters. The reflux rate is adjusted based on changes in the flash flow rate. For example, as flash flow rate increases, reflux rate may be adjusted for the greater amount of flow entering the flash vessel. The greater amount of flow may also have a subsequent effect on flow into the light ends column and decanter liquid level. In some cases, the processes may comprise the step of controlling the liquid level in the decanter based on at least one of flash flow rate and reflux rate, e.g., based on the flash flow rate, based on the reflux rate, or based on both the flash flow rate and the reflux rate. The variances in sidedraw concentrations are improved. For example, the water concentration in the sidedraw may vary by +/−0.3%, under steady state operation, e.g., +/−0.2% or +/−0.1%, and/or the water concentration in the sidedraw may range from 1.1 wt % to 3 wt %, e.g., from 1.3 wt % to 2.7 wt % or from 1.5 wt % to 2.5 wt %.

In some embodiments, the control schemes of the inventive processes provide a liquid level in the decanter that is substantially constant, under steady state operation for at least 6 hours, e.g., at least 12 hours or at least 24 hours. For example, the liquid level may vary by +/−5%, e.g., +/−4%, +/−3%, +/−2%, +/−1%, +/−0.5%, or +/−0.2%, during this time period.

In one embodiment, the controlling comprises measuring the liquid level in the decanter and adjusting the flash flow rate (and/or the reflux rate) in response to the liquid level. The measured level may be compared to a predetermined level and the adjusting of the flash flow rate (and/or the reflux rate) may be based on this comparison. For example, if the liquid level has increased past the predetermined level, the controlling may comprise decreasing the flash flow rate (and/or increasing the reflux rate). As a result, an decreased flow rate of liquid will be directed to the flash vessel (and to subsequent units), thus causing the liquid level to decrease. The decreased flow rate may be maintained until the liquid level returns to the predetermined level (within a margin of error). Thus, the controlling may comprise decreasing the flash flow rate if the liquid level increases.

In one embodiment, the controlling may comprise increasing the flash flow rate (and/or decreasing the reflux rate) if the liquid level decreases. The measured level may be compared to a predetermined level and the adjusting of the flash flow rate (and/or the reflux rate) may be based on this comparison. For example, if the liquid level has decreased below the predetermined level, the controlling may comprise increasing the flash flow rate (and/or decreasing the reflux rate). As a result, an increased flow rate of liquid will be directed to the flash vessel (and to subsequent units), thus causing the liquid level to increase. The increased flow rate may be maintained until the liquid level returns to the predetermined level (within a margin of error).

In one embodiment, the processes comprise the steps of: carbonylating at least one reactant selected from the group consisting of methanol, dimethyl ether, methyl acetate, and mixtures thereof, in the presence of a metal catalyst, methyl iodide, a halide salt, and optionally a finite amount water, to form a crude acetic acid product; conveying the crude acetic acid product to a flash vessel at a flash flow rate; flashing the crude acetic acid product to form a first vapor stream comprising acetic acid and methyl iodide and a first liquid residue stream comprising metal catalyst and halide salt; separating, in a light ends column, the flashed first vapor stream to form a second vapor stream comprising methyl iodide and optionally acetaldehyde, a sidedraw comprising purified acetic acid product and optionally water, and a second liquid residue stream; condensing, in a decanter, at least a portion of the second vapor stream to form at least one liquid phase; refluxing to the light ends column at least a portion of the at least one liquid phase at a reflux rate; and controlling a liquid level in the decanter based on at least one of flash flow rate and reflux rate; wherein the reflux rate is adjusted based on changes in the flash flow rate and/or wherein the controlling comprises measuring the flash flow rate and adjusting the reflux rate in response to the measuring.

In one embodiment, the processes comprise the steps of: carbonylating at least one reactant selected from the group consisting of methanol, dimethyl ether, methyl acetate, and mixtures thereof, in the presence of a metal catalyst, methyl iodide, a halide salt, and optionally a finite amount water, to form a crude acetic acid product; conveying the crude acetic acid product to a flash vessel at a flash flow rate; flashing the crude acetic acid product to form a first vapor stream comprising acetic acid and methyl iodide and a first liquid residue stream comprising metal catalyst and halide salt; separating, in a light ends column, the flashed first vapor stream to form a second vapor stream comprising methyl iodide and optionally acetaldehyde, a sidedraw comprising purified acetic acid product and optionally water, and a second liquid residue stream; condensing, in a decanter, at least a portion of the second vapor stream to form at least one liquid phase; refluxing to the light ends column at least a portion of the at least one liquid phase at a reflux rate; wherein the reflux rate is adjusted based on changes in the flash flow rate; and wherein the water concentration in the sidedraw varies by +/−0.3%, under steady state operation and/or the water concentration in the sidedraw ranges from 1.1 wt % to 3 wt %.

In one embodiment, the processes comprise the steps of: carbonylating at least one reactant selected from the group consisting of methanol, dimethyl ether, methyl acetate, and mixtures thereof, in the presence of a metal catalyst, methyl iodide, a halide salt, and optionally a finite amount water, to form a crude acetic acid product; conveying the crude acetic acid product to a flash vessel at a flash flow rate; flashing the crude acetic acid product to form a first vapor stream comprising acetic acid and methyl iodide and a first liquid residue stream comprising metal catalyst and halide salt; separating, in a light ends column, the flashed first vapor stream to form a second vapor stream comprising methyl iodide and optionally acetaldehyde, a sidedraw comprising purified acetic acid product and optionally water, and a second liquid residue stream; condensing, in a decanter, at least a portion of the second vapor stream to form at least one liquid phase; refluxing to the light ends column at least a portion of the at least one liquid phase at a reflux rate; wherein the reflux rate is adjusted based on changes in the flash flow rate; and wherein the at least one liquid phase comprises at least a portion of the heavy phase and the specific gravity of the heavy phase varies by +/−0.05, under steady state operation and/or the specific gravity of the heavy phase ranges from 1.5 to 1.8, under steady state operation.

In one embodiment, the processes comprise the steps of: carbonylating at least one reactant selected from the group consisting of methanol, dimethyl ether, methyl acetate, and mixtures thereof, in the presence of a metal catalyst, methyl iodide, a halide salt, and optionally a finite amount water, to form a crude acetic acid product; conveying the crude acetic acid product to a flash vessel at a flash flow rate; flashing the crude acetic acid product to form a first vapor stream comprising acetic acid and methyl iodide and a first liquid residue stream comprising metal catalyst and halide salt; separating, in a light ends column, the flashed first vapor stream to form a second vapor stream comprising methyl iodide and optionally acetaldehyde, a sidedraw comprising purified acetic acid product and optionally water, and a second liquid residue stream; condensing, in a decanter, at least a portion of the second vapor stream to form at least one liquid phase; refluxing to the light ends column at least a portion of the at least one liquid phase at a reflux rate; and directing a second portion of the at least one liquid phase to a PRC removal system at a PRS feed rate; wherein the reflux rate is adjusted based on changes in the flash flow rate; and optionally wherein the PRS feed rate varies by +/−25%, under steady state operation.

In one embodiment, the processes comprise the steps of: carbonylating at least one reactant selected from the group consisting of methanol, dimethyl ether, methyl acetate, and mixtures thereof, in the presence of a metal catalyst, methyl iodide, a halide salt, and optionally a finite amount water, to form a crude acetic acid product; conveying the crude acetic acid product to a flash vessel at a flash flow rate; flashing the crude acetic acid product to form a first vapor stream comprising acetic acid and methyl iodide and a first liquid residue stream comprising metal catalyst and halide salt; separating, in a light ends column, the flashed first vapor stream to form a second vapor stream comprising methyl iodide and optionally acetaldehyde, a sidedraw comprising purified acetic acid product and optionally water, and a second liquid residue stream; condensing, in a decanter, at least a portion of the second vapor stream to form at least one liquid phase; refluxing to the light ends column at least a portion of the at least one liquid phase at a reflux rate; wherein the reflux rate is adjusted based on changes in the flash flow rate; and wherein the at least one liquid phase comprises at least a portion of the light phase and the specific gravity of the light phase varies by +/−0.05, under steady state operation and/or the specific gravity of the light phase ranges from 0.9 to 1.2, under steady state operation.

In some embodiments, the processes comprise the step of carbonylating at least one reactant selected from the group consisting of methanol, dimethyl ether, methyl acetate, and mixtures thereof, preferably methanol, in a reaction medium comprising a metal catalyst, methyl iodide, a halide salt, and optionally a finite amount water, to form a crude acetic acid product. The crude acetic acid product is flashed, with or without heat, to form a first vapor stream and a first liquid residue stream. The first vapor stream comprises acetic acid and methyl iodide. The first liquid residue stream comprises metal catalyst and halide salt and may be recycled to the reactor. The flashed first vapor stream is separated in a light ends column to form a second vapor stream, a sidedraw, and a second liquid residue stream. The second vapor stream comprises methyl iodide and optionally acetaldehyde. The sidedraw comprises purified acetic acid product and water. The second residue stream comprises acetic acid, water, and catalyst and may be recycled to the reactor. At least a portion of the second vapor stream is condensed in a decanter to form at least one liquid phase. The at least one liquid phase, in some embodiments, comprises a light phase. In some embodiments, the at least one liquid phase comprises a heavy phase. In some embodiments the at least one liquid phase comprises both a light liquid phase and a heavy phase. A liquid level is established in the decanter by the condensation of the second vapor stream. The liquid level is maintained so as to avoid upsets or overflows of the decanter. At least a portion of the at least one liquid phase is refluxed to the light ends column, thus establishing a reflux loop. In some cases, the light phase is refluxed to establish the reflux loop. In some cases, the heavy phase is refluxed to establish the reflux loop. It is also contemplated that both the heavy phase and the light phase are refluxed to establish the reflux loop(s). The reflux loop has a reflux rate, which is the flow rate at which the at least one liquid phase is returned to the light ends column. The process further comprises the step of controlling the liquid level in the decanter via the reflux rate of the reflux loop. Preferably, the liquid level in the decanter is controlled such that the liquid level is substantially constant, under steady state operation, and, importantly, the water content in the reactor may be maintained at a substantially constant level, under steady state operation. The variances in sidedraw concentrations are improved. For example, the water concentration in the sidedraw may vary by +/−0.3%, under steady state operation, e.g., +/−0.2% or +/−0.1%, and/or the water concentration in the sidedraw may range from 1.1 wt % to 3 wt %, e.g., from 1.3 wt % to 2.7 wt % or from 1.5 wt % to 2.5 wt %.

In one embodiment, the controlling comprises measuring the liquid level in the decanter and adjusting the reflux rate in response to the liquid level. The measured level may be compared to a predetermined level and the adjusting of the reflux rate may be based on this comparison. For example, if the liquid level has increased past the predetermined level, the controlling may comprise increasing the reflux rate. As a result, an increased flow rate of liquid will be withdrawn from the decanter (to the light ends column), thus causing the liquid level to decrease. The increased flow rate may be maintained until the liquid level returns to the predetermined level (within a margin of error). Thus, the controlling may comprise increasing the reflux rate if the liquid level increases.

In one embodiment, the controlling may comprise decreasing the reflux rate if the liquid level decreases. The measured level may be compared to a predetermined level and the adjusting of the reflux rate may be based on this comparison. For example, if the liquid level has decreased below the predetermined level, the controlling may comprise decreasing the reflux rate. As a result, a decreased flow rate of liquid will be withdrawn from the decanter (to the light ends column), thus causing the liquid level to increase. The decreased flow rate may be maintained until the liquid level returns to the predetermined level (within a margin of error).

In one embodiment, the processes comprise the steps of: carbonylating at least one reactant selected from the group consisting of methanol, dimethyl ether, methyl acetate, and mixtures thereof, in the presence of a metal catalyst, methyl iodide, a halide salt, and optionally a finite amount water, to form a crude acetic acid product; flashing the crude acetic acid product to form a first vapor stream comprising acetic acid and methyl iodide and a first liquid residue stream comprising metal catalyst and halide salt; separating, in a light ends column, the flashed vapor stream to form a second vapor stream comprising methyl iodide and optionally acetaldehyde, a sidedraw comprising purified acetic acid product and water, and a second liquid residue stream; condensing, in a decanter, at least a portion of the second vapor stream to form at least one liquid phase; refluxing to the light ends column at least a portion of the at least one liquid phase at a reflux rate; controlling a liquid level in the decanter by adjusting or controlling the reflux rate; wherein the water concentration in the sidedraw ranges from 1.1 wt % to 3 wt %.

In one embodiment, the processes comprise the steps of: carbonylating at least one reactant selected from the group consisting of methanol, dimethyl ether, methyl acetate, and mixtures thereof, in the presence of a metal catalyst, methyl iodide, a halide salt, and optionally a finite amount water, to form a crude acetic acid product; flashing the crude acetic acid product to form a first vapor stream comprising acetic acid and methyl iodide and a first liquid residue stream comprising metal catalyst and halide salt; separating, in a light ends column, the flashed vapor stream to form a second vapor stream comprising methyl iodide and optionally acetaldehyde, a sidedraw comprising purified acetic acid product and water, and a second liquid residue stream; condensing, in a decanter, at least a portion of the second vapor stream to form at least one liquid phase; refluxing to the light ends column at least a portion of the at least one liquid phase at a reflux rate; controlling a liquid level in the decanter by adjusting or controlling the reflux rate; wherein the liquid level in the decanter varies by +/−5%, under steady state operation.

In one embodiment, the processes comprise the steps of: carbonylating at least one reactant selected from the group consisting of methanol, dimethyl ether, methyl acetate, and mixtures thereof, in the presence of a metal catalyst, methyl iodide, a halide salt, and optionally a finite amount water, to form a crude acetic acid product; flashing the crude acetic acid product to form a first vapor stream comprising acetic acid and methyl iodide and a first liquid residue stream comprising metal catalyst and halide salt; separating, in a light ends column, the flashed vapor stream to form a second vapor stream comprising methyl iodide and optionally acetaldehyde, a sidedraw comprising purified acetic acid product and water, and a second liquid residue stream; condensing, in a decanter, at least a portion of the second vapor stream to form at least one liquid phase; refluxing to the light ends column at least a portion of the at least one liquid phase at a reflux rate; controlling a liquid level in the decanter by adjusting or controlling the reflux rate; wherein the water concentration in the sidedraw varies by +/−0.3%, and wherein the at least one liquid phase comprises a heavy phase and the specific gravity of the heavy phase ranges from 1.5 to 1.8, under steady state operation and/or wherein the at least one liquid phase comprises a heavy phase and the specific gravity of the heavy phase varies by +/−0.05, under steady state operation.

In one embodiment, the processes comprise the steps of: carbonylating at least one reactant selected from the group consisting of methanol, dimethyl ether, methyl acetate, and mixtures thereof, in the presence of a metal catalyst, methyl iodide, a halide salt, and optionally a finite amount water, to form a crude acetic acid product; flashing the crude acetic acid product to form a first vapor stream comprising acetic acid and methyl iodide and a first liquid residue stream comprising metal catalyst and halide salt; separating, in a light ends column, the flashed vapor stream to form a second vapor stream comprising methyl iodide and optionally acetaldehyde, a sidedraw comprising purified acetic acid product and water, and a second liquid residue stream; condensing, in a decanter, at least a portion of the second vapor stream to form at least one liquid phase; refluxing to the light ends column at least a portion of the at least one liquid phase at a reflux rate; controlling a liquid level in the decanter by adjusting or controlling the reflux rate; wherein the water concentration in the sidedraw varies by +/−0.3%, and wherein the at least one liquid phase comprises a light phase and the specific gravity of the light phase varies by +/−0.05, under steady state operation and/or wherein the at least one liquid phase comprises a light phase and the specific gravity of the light phase ranges from 0.9 to 1.2, under steady state operation.

One advantageous aspect of the aforementioned processes is the use of the flash flow rate as a control mechanism to maintain consistent light ends column operations and/or the liquid level in the decanter. It is within the contemplation of the invention to employ the general principles of process control to implement the use of the flash flow rate (and optionally the use of the reflux loop) in this regard. The exemplary process control mechanisms disclosed herein are merely exemplary and are not intended to limit the scope of the invention. Other specific process control mechanisms are within the scope of the invention, as long as the flash flow rate (and optionally the reflux loop) is used to maintain consistent light ends column operations and/or the liquid level in the decanter.

Another advantageous aspect of the aforementioned processes is the use of the reflux loop as a control mechanism to maintain the liquid level in the decanter. It is within the contemplation of the invention to employ the general principles of process control to implement the use of the reflux loop in this regard. The exemplary process control mechanisms disclosed herein are merely exemplary and are not intended to limit the scope of the invention. Other specific process control mechanisms are within the scope of the invention, as long as the reflux loop is used to maintain the liquid level in the decanter.

As a result of the control schemes discussed herein, the light ends column may be capable of more consistent operation, e.g., a more consistent column profile is established and maintained. When the decanter level is controlled by flow out of the decanter, e.g., recycle to the reactor, the reflux remains constant, not variable. While this scheme may be somewhat effective to control some distillation columns, this scheme is far from optimal for many separation trains. Keeping the reflux constant in such a situation tends to amplify a column disturbance further and the capability of the tower to handle the disturbance may be exceeded. Any disturbance in the feed to the column that results in an increase in material in the overhead decanter, can best be handled by a corresponding increase in reflux, as discussed herein. Thus, by employing the control schemes disclosed herein, the streams exiting the light ends column will be more consistent, e.g., when operating at steady state. For example, the water concentration in the side draw exiting the light ends column is substantially constant, e.g., in accordance with the ranges and limits disclosed herein. The consistency of the water concentration in the side draw is an indicator of the consistency of the column operation, e.g., column profile. Without the light ends operation control and/or decanter liquid level control described herein, the side draw exiting the light ends column would be much less consistent.

In some embodiments, the control schemes of the inventive processes provide a liquid level in the decanter that is substantially constant, under steady state operation for at least 6 hours, e.g., at least 12 hours or at least 24 hours. For example, the liquid level may vary by +/−5%, e.g., +/−4%, +/−3%, +/−2%, +/−1%, +/−0.5%, or +/−0.2%, during this time period.

In one embodiment, the processes further comprise the step of directing at least some of the remainder of the at least one liquid phase to a permanganate reducing compound (PRC) removal system at a PRS feed rate. The PRS is utilized to remove PRCs, primarily aldehydes such as acetaldehyde, from a low-boiling overhead vapor stream of a light ends distillation column (a second vapor stream), e.g., from the light phase and/or the heavy phase. At least a portion of the at least one liquid phase may be directed to the PRS. The portion of the at least one liquid phase directed to the PRS is not the portion of the at least one liquid phase that is refluxed to the light ends column. As a result of the control schemes disclosed herein, the portion of the at least one liquid phase that is directed to the PRS is more consistent, both in quantity (PRS feed rate) and composition. In one embodiment, the PRS feed rate is substantially constant, under steady state operation. For example, the PRS feed rate may vary by +/−25%, e.g., +/−15%, +/−10%, +/−5%, or +/−3%. The consistency of the stream fed to the PRS provides for more consistent operation of the PRS.

In one embodiment, the at least one liquid phase comprises a light phase. In some cases, the light phase may be refluxed to the light ends column. In these cases the specific gravity of the light phase may, advantageously, be substantially constant, under steady state operation. For example, the specific gravity of the light phase varies by +/−0.15, e.g., +/−0.05, +/−0.03, e.g., or +/−0.01. In terms of ranges, the specific gravity of the light phase may be from 0.9 to 1.2, e.g., from 1.0 to 1.1, from 1.03 to 1.07, or from 1.04 to 1.06. The consistency of the specific gravity of the light phase is an indicator of the consistency of the column operation, e.g., column profile.

In one embodiment, the at least one liquid phase comprises a heavy phase. In some cases, the heavy phase may be refluxed to the light ends column. In these cases the specific gravity of the heavy phase may, advantageously, be substantially constant, under steady state operation. For example, the specific gravity of the heavy phase varies by +/−0.05, e.g., +/−0.03, e.g., or +/−0.01. In terms of ranges, the specific gravity of the heavy phase may be from 1.5 to 1.8, from 1.55 to 1.75, or from 1.6 to 1.7. The consistency of the specific gravity of the heavy phase is an indicator of the consistency of the column operation, e.g., column profile. If the tower profile were to rise, the heavy phase density would drop.

In one embodiment, the sidedraw may be further processed, e.g., dehydrated or dried, in a drying column to form a dehydrated acetic acid product comprising acetic acid and a minor amount of water. As noted above, the water concentration in the side draw fed to the drying column will, beneficially, be substantially constant as a result of the control schemes disclosed herein. Thus, disturbances to the tower profile are minimized and, hence, the side draw composition remains more consistent than when the reflux is held constant and the tower composition profile is allowed to fluctuate. The consistency of the stream fed to the drying column allows for a more consistent profile in the drying column, which in turn provides for improved separation efficiency. In one embodiment, as a result of the control schemes disclosed herein, the amount hydrogen iodide fed to the drying column will be reduced, as compared to a similar stream resulting from process that does not maintain decanter liquid level via the reflux rate or flash flow rate.

In one embodiment, the processes of the present invention allow for separation balance between the light ends column and the drying column. As noted above, the use of the control schemes disclosed herein results in more steady operation of the light ends tower and more consistent composition profiles in the light ends tower. These consistencies, in turn, allow a broader range of light phase recycle to the reactor to be managed. The composition of the side stream can be more readily controlled as well. One benefit of these operations is that the overall separation of water from product acetic acid can be balanced between the two columns, as opposed to just one, for optimal performance within the constraints of the actual operating equipment.

"Steady state operation" is a well-known term in the art. Steady state operation means that the parameters of a particular operation are constant over time (or vary only nominally). For example, for column operations, steady state means that the total of streams going into an operation is equal to the total flow of streams exiting an operation. Steady state does not refer to start-up or shut-down periods. As used herein, the term "under steady state operation" can be interpreted as under steady state operations for at least 6 hours, e.g., at least 12 hours, at least 24 hours, or at least 48 hours.

Acetic Acid Production Systems

An exemplary acetic acid production process is described below. In the interest of clarity, not all features of an actual implementation are described in this specification. The process description is merely exemplary and is not meant to limit the scope of the invention.

The carbonylation reaction of methanol to acetic acid product may be carried out by contacting the methanol feed with gaseous carbon monoxide bubbled through an acetic acid solvent reaction medium containing the metal catalyst, e.g., rhodium catalyst, a halogen-containing catalyst promoter, e.g., methyl iodide, additional soluble halide salt, e.g., iodide salt such as lithium iodide, and optionally methyl acetate and/or water, at conditions of temperature and pressure suitable to form the carbonylation product.

The catalyst may be a Group VIII metal catalyst, such as rhodium, and a halogen-containing catalyst promoter. A particularly useful process is the low water rhodium-catalyzed carbonylation of methanol to acetic acid as exemplified in U.S. Pat. No. 5,001,259. Other metal catalysts, e.g., iridium-based catalysts, are contemplated as well. Generally, the metal component, e.g., rhodium component, of the catalyst system is believed to be present in the form of a coordination compound of rhodium with a halogen component providing at least one of the ligands of such coordination compound. In addition to the coordination of rhodium and halogen, it is also believed that carbon monoxide will coordinate with rhodium. The rhodium component of the catalyst system may be provided by introducing into the reaction zone rhodium in the form of rhodium metal, rhodium salts such as the oxides, acetates, iodides, carbonates, hydroxides, chlorides, etc., or other compounds that result in the formation of a coordination compound of rhodium in the reaction environment. The metal catalyst, e.g., rhodium catalyst, is, in some embodiments, present in amounts from 200 to 2000 weight parts per million (wppm).

The halogen-containing catalyst promoter of the catalyst system consists of a halogen compound comprising an organic halide. Thus, alkyl, aryl, and substituted alkyl or aryl halides can be used. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter will include methyl halide, and more preferably methyl iodide.

It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or other cations such as those based on amine or phosphine compounds (optionally, ternary or quaternary cations), can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable. In the low water carbonylation process, the additional iodide ion over and above the iodide ion present as hydrogen iodide is generally present in the catalyst solution in amounts such that the total iodide ion concentration is from 2 to 20 wt. % and the methyl acetate is generally present in amounts from 0.5 to 30 wt. %, and the methyl iodide is generally present in amounts from 5 to 20 wt. %.

In some embodiments, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. A desired ester is methyl acetate. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The absolute concentration of iodide ion content provided as merely an example, and is not to be interpreted as limiting.

In embodiments, the process for producing acetic acid further includes introducing a lithium compound into the reactor to maintain the concentration of lithium acetate in an amount from 0.3 to 0.7 wt % in the reaction medium. In embodiments, an amount of the lithium compound is introduced into the reactor to maintain the concentration of hydrogen iodide in an amount from 0.1 to 1.3 wt % in the reaction medium. In embodiments, the concentration of the rhodium catalyst is maintained in an amount from 200 to 3000 wppm in the reaction medium, the concentration of water is maintained in amount from 0.1 to 4.1 wt % in the reaction medium, and the concentration of methyl acetate is maintained from 0.6 to 4.1 wt % in the reaction medium, based on the total weight of the reaction medium present within the carbonylation reactor.

In embodiments, the lithium compound introduced into the reactor is selected from the group consisting of lithium acetate, lithium carboxylates, lithium carbonates, lithium hydroxide, other organic lithium salts, and mixtures thereof. In embodiments, the lithium compound is soluble in the reaction medium. In an embodiment, lithium acetate dihydrate may be used as the source of the lithium compound.

Lithium acetate reacts with hydrogen iodide according to the following equilibrium reaction (I) to form lithium iodide and acetic acid:

$$\text{LiOAc} + \text{HI} \leftrightarrow \text{LiI} + \text{HOAc} \quad (I)$$

Lithium acetate is thought to provide improved control of hydrogen iodide concentration relative to other acetates, such as methyl acetate, present in the reaction medium. Without being bound by theory, lithium acetate is a conjugate base of acetic acid and thus reactive toward hydrogen iodide via an acid-base reaction. This property is thought to result in an equilibrium of the reaction (I) which favors reaction products over and above that produced by the corresponding equilibrium of methyl acetate and hydrogen iodide. This improved equilibrium is favored by water concentrations of less than 4.1 wt % in the reaction medium. In addition, the relatively low volatility of lithium acetate compared to methyl acetate allows the lithium acetate to remain in the reaction medium except for volatility losses and small amounts of entrainment into the vapor crude product. In contrast, the relatively high volatility of methyl acetate allows the material to distill into the purification train, rendering methyl acetate more difficult to control. Lithium acetate is much easier to maintain and control in the process at consistent low concentrations of hydrogen iodide. Accordingly, a relatively small amount of lithium acetate may be employed relative to the amount of methyl acetate needed to control hydrogen iodide concentrations in the reaction medium. It has further been discovered that lithium acetate is at least three times more effective than methyl acetate in promoting methyl iodide oxidative addition to the rhodium [I] complex.

In embodiments, the concentration of lithium acetate in the reaction medium is maintained at greater than or equal to 0.3 wt. %, or greater than or equal to 0.35 wt. %, or greater than or equal to 0.4 wt. %, or greater than or equal to 0.45 wt. %, or greater than or equal to 0.5 wt. %, and/or in embodiments, the concentration of lithium acetate in the reaction medium is maintained at less than or equal to 0.7 wt. %, or less than or equal to 0.65 wt. %, or less than or equal to 0.6 wt. %, or less than or equal to 0.55 wt. %.

It has been discovered that an excess of lithium acetate in the reaction medium can adversely affect the other compounds in the reaction medium, leading to decrease productivity. Conversely, it has been discovered that a lithium acetate concentration in the reaction medium below about 0.3 wt. % is unable to maintain the desired hydrogen iodide concentrations in the reaction medium of below 1.3 wt. %.

In embodiments, the lithium compound may be introduced continuously or intermittently into the reaction medium. In embodiments, the lithium compound is introduced during reactor start up. In embodiments, the lithium compound is introduced intermittently to replace entrainment losses.

The reaction medium may also contain impurities that should be controlled to avoid byproduct formation. One impurity in the reaction medium may be ethyl iodide, which is difficult to separate from acetic acid. Applicant has further discovered that the formation of ethyl iodide may be affected by numerous variables, including the concentration of acetaldehyde, ethyl acetate, methyl acetate and methyl iodide in the reaction medium. Additionally, ethanol content in the methanol source, hydrogen partial pressure and hydrogen content in the carbon monoxide source have been discovered to affect ethyl iodide concentration in the reaction medium and, consequently, propionic acid concentration in the final acetic acid product.

In embodiments, the propionic acid concentration in the acetic acid product may further be maintained below 250 wppm by maintaining the ethyl iodide concentration in the reaction medium at less than or equal to 750 wppm without removing propionic acid from the acetic acid product.

In embodiments, the ethyl iodide concentration in the reaction medium and propionic acid in the acetic acid product may be present in a weight ratio from 3:1 to 1:2. In embodiments, the acetaldehyde:ethyl iodide concentration in the reaction medium is maintained at a weight ratio from 2:1 to 20:1.

In embodiments, the ethyl iodide concentration in the reaction medium may be maintained by controlling at least one of the hydrogen partial pressure, the methyl acetate concentration, the methyl iodide concentration, and/or the acetaldehyde concentration in the reaction medium.

In embodiments, the concentration of ethyl iodide in the reaction medium is maintained/controlled to be less than or equal to 750 wppm, or e.g., less than or equal to 650 wppm, or less than or equal to 550 wppm, or less than or equal to 450 wppm, or less than or equal to 350 wppm. In embodiments, the concentration of ethyl iodide in the reaction medium is maintained/controlled at greater than or equal to 1 wppm, or e.g., 5 wppm, or 10 wppm, or 20 wppm, or 25 wppm, and less than or equal to 650 wppm, or e.g., 550 wppm, or 450 wppm, or 350 wppm.

In embodiments, the weight ratio of ethyl iodide in the reaction medium to propionic acid in the acetic acid product may range from 3:1 to 1:2, or e.g., from 5:2 to 1:2, or from 2:1 to 1:2, or from 3:2 to 1:2.

In embodiments, the weight ratio of acetaldehyde to ethyl iodide in the reaction medium may range from 20:1 to 2:1, or e.g., from 15:1 to 2:1 or from 9:1 to 2:1.

In one embodiment, the gaseous purge stream 106 contains low amounts of hydrogen iodide of less than or equal to 1 wt. %, e.g., less than or equal to 0.9 wt. %, less than or equal to 0.8 wt. %, less than or equal to 0.7 wt. %, less than or equal to 0.5 wt. %. Hydrogen iodide in excess of these amounts may increase the duty on the scrubber to prevent hydrogen iodide from being purged.

In one embodiment, a suitable potassium permanganate test is JIS K1351 (2007).

The liquid reaction medium employed may include any solvent compatible with the catalyst system and may include pure alcohols, or mixtures of the alcohol feedstock and/or the desired carboxylic acid and/or esters of these two compounds. A preferred solvent and liquid reaction medium for the low water carbonylation process contains the desired carboxylic acid product. Thus, in the carbonylation of methanol to acetic acid, a preferred solvent system contains acetic acid.

Water is contained in the reaction medium but desirably at low concentrations for achieving sufficient reaction rates. It has previously been taught, e.g., in U.S. Pat. No. 3,769,329, that in rhodium-catalyzed carbonylation reactions, the addition of water exerts a beneficial effect upon the reaction rate. Thus, some commercial operations are commonly run at water concentrations of greater than 14 wt. %. However, in some embodiments, water concentrations less than or equal to 14 wt. %, e.g., less than or equal to 10 wt. %, less than or equal to 1 wt. % or less than or equal to 0.1 wt. %, may be utilized. In terms of ranges, the reaction medium may comprise from 0.1 wt % to 14 wt % water, e.g., from 0.2 wt % to 10 wt % or from 0.25 wt % to 5 wt %, based on the total weight of the reaction medium.

Typical reaction temperatures for carbonylation may be from 150 to 250° C., with the temperature range of 180 to 225° C. being a preferred range. The carbon monoxide partial pressure in the reactor can vary widely but is typically from 2 to 30 atmospheres, e.g., from 3 to 10 atmospheres. Because of the partial pressure of by-products and the vapor pressure of the contained liquids, the total reactor pressure may range from 15 to 40 atmospheres.

An exemplary reaction and acetic acid recovery system 100 is shown in FIG. 1. As shown, methanol feed stream 101 and carbon monoxide-containing feed stream 102 are directed to liquid phase carbonylation reactor 104, in which the carbonylation reaction occurs to form acetic acid.

Carbonylation reactor 104 is preferably either a stirred vessel or bubble-column type vessel, with or without an agitator, within which the reacting liquid or slurry contents are maintained, preferably automatically, a predetermined level, which preferably remains substantially constant during normal operation. Into carbonylation reactor 104, the methanol composition, carbon monoxide, and sufficient water are continuously introduced as needed to maintain at least a finite concentration of water, e.g., 0.1 wt. %., in the reaction medium.

In a typical carbonylation process, carbon monoxide is continuously introduced into the carbonylation reactor, desirably below the agitator, which may be used to stir the contents. The gaseous feed preferably is thoroughly dispersed through the reacting liquid by this stirring means. Gaseous purge stream 106 desirably is vented from reactor 104 to prevent buildup of gaseous by-products and to maintain a set carbon monoxide partial pressure at a given total reactor pressure. The temperature of the reactor may be controlled and the carbon monoxide feed is introduced at a rate sufficient to maintain the desired total reactor pressure. Stream 113 comprising a crude, unflashed acetic acid product exits reactor 104.

The crude acetic acid product may be purified in separation zone 108 to recover the acetic acid and recycle catalyst solution, methyl iodide, methyl acetate, and other system components within the process. Thus, a recycled catalyst solution, such as stream 110 from flash vessel 112, and optionally one or more of recycle streams 114, 116, 118, and 120, also are introduced into the reactor 104. Of course, one or more of the recycle streams may be combined prior to being introduced into the reactor 104. As noted above, however, in view of the control schemes disclosed herein, the use of these recycle streams for process control may be reduced or eliminated. In some cases, however, these recycle streams may be utilized purely to return components to the reactor.

Crude product is drawn off from the carbonylation reactor 104 at a rate sufficient to maintain a constant level therein and is provided to flash vessel 112 via stream 113. In flash vessel 112, the crude product is separated in a flash separation step to obtain a volatile ("vapor") overhead stream (a first vapor stream) 122 comprising acetic acid and a less volatile (liquid) residue stream 110 comprising a catalyst-containing solution (predominantly acetic acid containing the rhodium and the iodide salt along with lesser quantities of methyl acetate, methyl iodide, and water), which preferably is recycled to the reactor, as discussed above. Thus, the purification of the crude acetic acid product may comprise the steps of flashing the crude acetic acid product, with or without heat, to form the first vapor stream (stream 122) comprising acetic acid and residual carbon monoxide and the first liquid residue stream (stream 110) comprising catalyst and recycling the first liquid residue to the first reactor.

In one embodiment, the vapor product stream comprises acetic acid, methyl iodide, methyl acetate, water, acetaldehyde, and hydrogen iodide. In one embodiment, the vapor product stream comprises acetic acid in an amount from 45 to 75 wt. %, methyl iodide in an amount from 20 to 50 wt. %, methyl acetate in an amount of less than or equal to 9 wt. %, and water in an amount of less than or equal to 15 wt. %, based on the total weight of the vapor product stream. In another embodiment, the vapor product stream comprises acetic acid in an amount from 45 to 75 wt. %, methyl iodide in an amount from 24 to less than 36 wt. %, methyl acetate in an amount of less than or equal to 9 wt. %, and water in an amount of less than or equal to 15 wt. %, based on the total weight of the vapor product stream. More preferably, the vapor product stream comprises acetic acid in an amount from 55 to 75 wt. %, methyl iodide in an amount from 24 to 35 wt. %, methyl acetate in an amount from 0.5 to 8 wt. %, and water in an amount from 0.5 to 14 wt. %. In yet a further preferred embodiment, the vapor product stream comprises acetic acid in an amount from 60 to 70 wt. %, methyl iodide in an amount from 25 to 35 wt. %, methyl acetate in an amount from 0.5 to 6.5 wt. %, and water in an amount from 1 to 8 wt. %. The acetaldehyde concentration in the vapor product stream may be in an amount from 0.005 to 1 wt. %, based on the total weight of the vapor product stream, e.g., from 0.01 to 0.8 wt. %, or from 0.01 to 0.7 wt. %. In some embodiments the acetaldehyde may be present in amounts less than or equal to 0.01 wt. %. The vapor product stream may comprise hydrogen iodide in an amount less than or equal to 1 wt. %, based on the total weight of the vapor product stream, e.g., less than or equal to 0.5 wt. %, or less than or equal to 0.1 wt. %. Hydrogen iodide is preferably present in the vapor product stream. The vapor product stream is preferably substantially free of, e.g., contains less than or equal to 0.0001 wt. %, propionic acid, based on the total weight of the vapor product stream.

The liquid recycle stream comprises acetic acid, the metal catalyst, corrosion metals, as well as other various compounds. In one embodiment, liquid recycle stream comprises acetic acid in an amount from 60 to 90 wt. %, metal catalyst in an amount from 0.01 to 0.5 wt. %; corrosion metals (e.g., nickel, iron and chromium) in a total amount from 10 to 2500 wppm; lithium iodide in an amount from 5 to 20 wt. %; methyl iodide in an amount from 0.5 to 5 wt. %; methyl acetate in an amount from 0.1 to 5 wt. %; water in an amount from 0.1 to 8 wt. %; acetaldehyde in an amount of less than or equal to 1 wt. % (e.g., from 0.0001 to 1 wt. % acetaldehyde); and hydrogen iodide in an amount of less than or equal to 0.5 wt. % (e.g., from 0.0001 to 0.5 wt. % hydrogen iodide).

The overhead stream from flash vessel 112 is directed to the light ends column 124 as stream 122, where distillation yields a low-boiling overhead vapor stream 126, a purified acetic acid product that preferably is removed via a sidedraw 128, and a high boiling residue stream 116. Acetic acid removed via sidedraw 128 preferably is subjected to further purification, such as in drying column 130 for selective separation of acetic acid from water. Thus, the purification may further comprise the step of separating, in a light ends column, the flashed vapor stream to form a second vapor stream (stream 126) comprising carbon monoxide, a sidedraw (stream 128) comprising purified acetic acid product, and a second liquid residue stream (stream 116).

It has been disclosed in U.S. Pat. Nos. 6,143,930 and 6,339,171 that there is generally a higher concentration of the PRCs, and in particular acetaldehyde concentration, in the low-boiling overhead vapor stream exiting the light ends column than in the high-boiling residue stream exiting the column. Thus, in some cases, low-boiling overhead vapor stream 126, containing PRCs, is subjected to additional processing in PRS 132 to reduce and/or remove the amount of PRCs present. As shown, low-boiling overhead vapor stream 126, therefore, is condensed and directed to an overhead phase separation unit, as shown by overhead receiver decanter 134. In addition to PRCs, low-boiling overhead vapor stream 126 may typically contain methyl iodide, methyl acetate, acetic acid, and water.

Conditions are desirably maintained in the process such that low-boiling overhead vapor stream 126, once in decanter 134, may separate to form at least one liquid phase, e.g., a light phase and/or a heavy phase. Generally, low-boiling overhead vapor stream 126 is cooled to a temperature sufficient to condense and separate the condensable methyl iodide, methyl acetate, acetaldehyde and other carbonyl components, and water to form two separate phases. A portion of stream 126 may include noncondensable gases such as carbon monoxide, carbon dioxide, hydrogen, and the like that can be vented as shown by stream 136 in FIG. 1, which may be directed to a low pressure absorber unit (not shown). The liquid phases in the decanter may establish liquid level 135 in decanter 134. Measuring device 137 is disposed in or around decanter 134. Measurement device 137 measures the liquid level. This liquid level may be utilized in the disclosed control schemes to control light ends column operation and/or decanter liquid level control. Preferably, measurement device 137 is in communication with other control hardware associated with the decanter (not shown). It is well within the purview of the art to select proper control hardware to implement the disclosed control schemes.

The condensed light phase in decanter 134 generally may comprise water, acetic acid, and PRCs, as well as quantities of methyl iodide and methyl acetate. The condensed light phase exits decanter 134 via line 131. The condensed heavy phase in decanter 134 may generally comprise methyl iodide, methyl acetate, and PRC's. The condensed heavy phase exits decanter via line 118. As shown in FIG. 1, at least a portion of the light phase and/or the heavy phase may be refluxed back to light ends column 124. A portion of the light phase in line 131 may be refluxed to light ends column 124 via line 131', thus establishing a reflux loop with line 126, decanter 134, line 131', and light ends column 124. A portion of the heavy phase in line 118 may be refluxed back to light ends column 124 via line 118' (with or without the light phase in line 131'), thus establishing a reflux loop with line 126, decanter 134, line 118', and light ends column 124. The reflux rate of streams 131' and/or 118' may be utilized to maintain the liquid level in decanter 134. Although streams 131' and 118' are indicated with solid lines, it is within the contemplation of the invention that only 131' or only 118' could be used in combination with line 126, decanter 134, and light ends column 124 to establish the reflux loop.

In addition to the portions of the light phase that may be refluxed 131', a separate portion of stream 131 may be directed to PRS 132. Stream 131" directs separate portion of stream 131 to PRS 132 via line 138. In addition to the heavy phase that may be refluxed, 118', a separate portion of stream 118 may be directed to PRS 132. Stream 118" directs a separate portion of stream 118 to PRS 132 after being combined with line 131" (optionally stream 118" could be directly fed to PRS 132. In view of the control schemes disclosed herein the composition of streams 118" and 131" may be more consistent, which will advantageously lead to more effective separations in PRS 132.

The condensed heavy liquid phase in the decanter 134 can be conveniently recirculated, either directly or indirectly, to the reactor 104 via stream 118, although this recirculation may not necessary for process control reasons. For example, a portion of this condensed heavy liquid phase can be recirculated to the reactor, with a slip stream (not shown), generally a small amount, e.g., from 5 to 40 vol. %, or from 5 to 20 vol. %, of the heavy liquid phase being directed to a PRS. This slip stream of the heavy liquid phase may be treated individually or may be combined with the condensed light liquid phase stream 138 for further distillation and extraction of carbonyl impurities.

Although the specific compositions of the light phase stream may vary widely, some preferred compositions are provided below in Table 1.

TABLE 1

Exemplary Light Liquid Phase from Light Ends Overhead

| | conc. (Wt. %) | conc. (Wt. %) | conc. (Wt. %) |
|---|---|---|---|
| Water | 40-80 | 50-75 | 70-75 |
| Methyl Acetate | 1-50 | 1-25 | 1-15 |
| Acetic Acid | 1-40 | 1-25 | 5-15 |
| PRC's | <5 | <3 | <1 |
| Methyl Iodide | <10 | <5 | <3 |

In one embodiment, the overhead decanter is arranged and constructed to maintain a low interface level to prevent an excess hold up of methyl iodide. Although the specific compositions of heavy liquid phase may vary widely, some exemplary compositions are provided below in Table 2.

TABLE 2

Exemplary Heavy Liquid Phase from Light Ends Overhead

| | conc. (Wt. %) | conc. (Wt. %) | conc. (Wt. %) |
|---|---|---|---|
| Water | 0.01-2 | 0.05-1 | 0.1-0.9 |
| Methyl Acetate | 0.1-25 | 0.5-20 | 0.7-15 |
| Acetic Acid | 0.1-10 | 0.2-8 | 0.5-6 |
| PRC's | <5 | <3 | <1 |
| Methyl Iodide | 40-98 | 50-95 | 60-85 |

The density of the heavy liquid phase 134 may be from 1.3 to 2, e.g., from 1.5 to 1.8, from 1.5 to 1.75 or from 1.55 to 1.7. As described in U.S. Pat. No. 6,677,480, the measured density in the heavy liquid phase 134 correlates with the methyl acetate concentration in the reaction medium. As density decreases, the methyl acetate concentration in the reaction medium increases. In one embodiment of the present invention, heavy liquid phase 134 is recycled to the reactor and the light liquid phase 133 is controlled to be recycled through the same pump. It may be desirable to recycle a portion of the light liquid phase 133 that does not disrupt the pump and maintains a density of the combined light liquid phase 133 and heavy liquid phase of greater than or equal to 1.3, e.g., greater than or equal to 1.4, greater than or equal to 1.5, or greater than or equal to 1.7. As described herein, a portion of the heavy liquid phase 134 may be treated to remove impurities such as acetaldehyde.

As shown in FIG. 1, the light phase exits decanter 134 via stream 131. A portion, e.g., aliquot portion, of light phase stream 131" is directed to PRS 132. Another portion, e.g., aliquot portion, of the light phase stream 131 optionally may be recycled to reactor 104 as shown by recycle stream 114, when additional water is desired or needed in reactor 104, although this recirculation may not necessary for process control reasons.

Light ends column 124 also preferably forms residuum or bottoms stream 116, which comprises primarily acetic acid and water. Since light ends bottoms stream 116 typically may comprise some residual catalyst, it may be beneficial to recycle all or a portion of light ends column residue stream 116 to reactor 104, although this recirculation may not necessary for process control reasons. Optionally, light ends column residue stream 116 may be combined with liquid residue stream 110 from flash vessel 112 and returned together to reactor 104, as shown in FIG. 1.

As indicated above, in addition to the overhead phase, light ends column 124 also forms an acetic acid sidedraw 128, which preferably comprises primarily acetic acid and water. In order to maintain an efficient product separation, it is important that the composition of sidedraw 128 does not vary or fluctuate significantly during normal operation. As previously discussed, the control schemes disclosed herein provide for improvements in the compositional consistency of sidedraw 128.

Optionally, a portion of sidedraw 128 may be recirculated to light ends column 124, preferably to a point below where sidedraw 128 was removed from light ends column 124, in order to improve the separation.

Since sidedraw 128 contains water in addition to acetic acid, sidedraw 128 from light ends column 124 preferably is directed to drying column 130, in which the acetic acid and water are separated from one another. Thus, the process may comprise the step of drying, in a drying column, the sidedraw (stream 128) to remove water therefrom. As shown, drying column 130, separates acetic acid sidedraw 128 to form overhead stream 144 comprised primarily of water and bottoms stream 146 comprised primarily of acetic acid. Overhead stream 144 preferably is cooled and condensed in a phase separation unit, e.g., decanter 148, to form a light phase and a heavy phase. As shown, a portion of the light phase is refluxed, as shown by streams 150 and 152 and the remainder of the light phase is returned to the reactor 104, as shown by stream 120. The heavy phase, which typically is an emulsion comprising water and methyl iodide, preferably is returned in its entirety to the reactor 104, as shown by stream 122, optionally after being combined with stream 120. Exemplary compositions for the light phase of the drying column overhead are provided below in Table 3.

TABLE 3

Exemplary Light Compositions from Drying Column Overhead

| | conc. (Wt. %) | conc. (Wt. %) | conc. (Wt. %) |
|---|---|---|---|
| HOAc | 1-20 | 1-15 | 1-10 |
| Water | 50-90 | 60-90 | 70-90 |
| MeI | <10 | <5 | <3 |
| MeAc | 1-20 | 1-15 | 1-10 |

Drying column bottoms stream 146 preferably comprises or consists essentially of acetic acid, with minor amounts of hydrogen iodide. In preferred embodiments, drying column bottoms stream 146 comprises acetic acid in an amount greater than 90 wt. %, e.g., greater than 95 wt. % or greater than 98 wt. %. Optionally, drying column bottoms stream 146 may be further processed, e.g., by passing through an ion exchange resin, prior to being stored or transported for commercial use.

Figure 2:
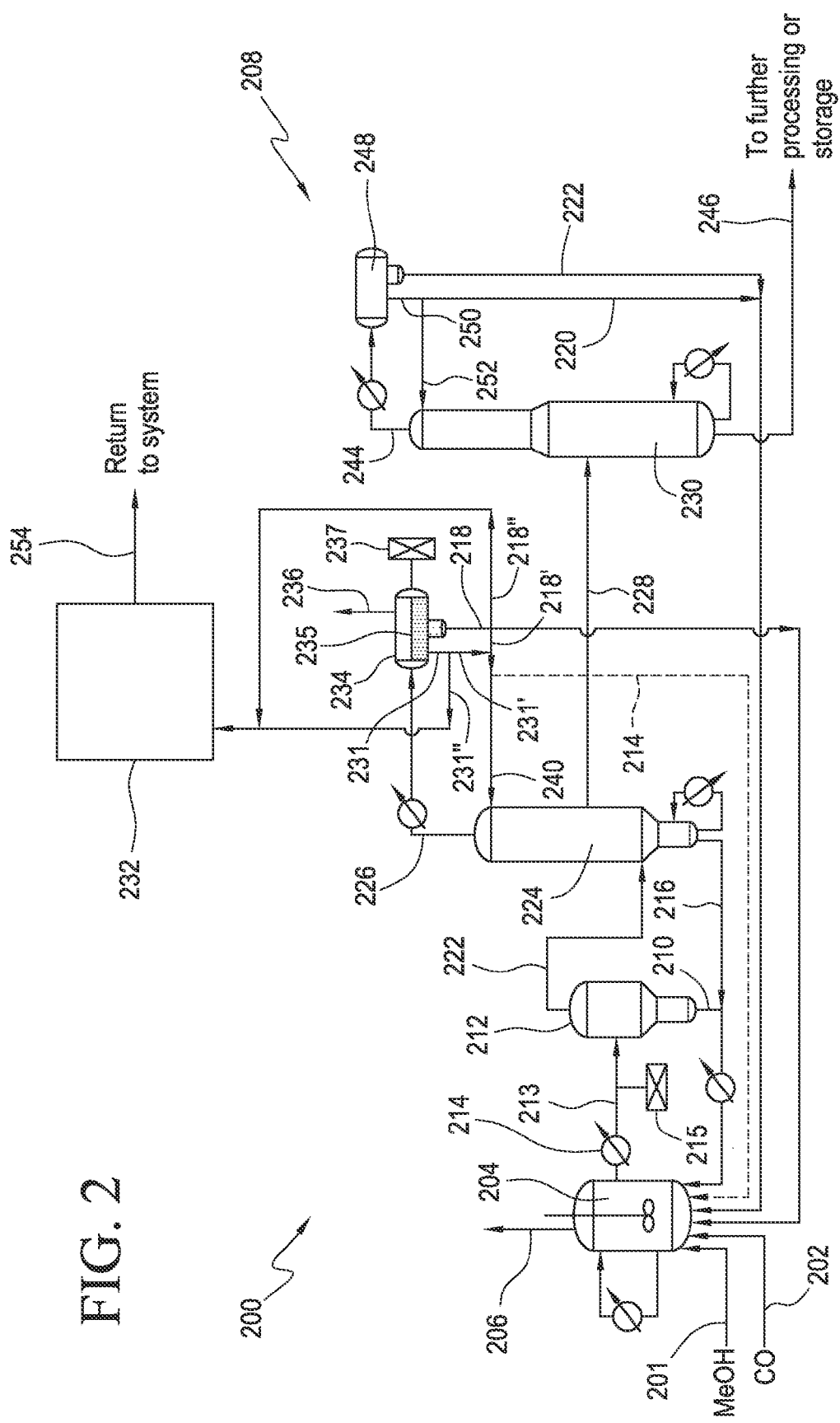
FIG. 2 shows a schematic of an acetic acid production process in accordance with the present invention.

Another reaction and acetic acid recovery system 200 is shown in FIG. 2. FIG. 2 shows many of the same components as FIG. 1, and like numbers reflect similar components operating in a similar manner. For example element 212 in FIG. 2 refers to a flash vessel that is similar to flash vessel 112 of FIG. 1 and operates in a manner similar to that of flash vessel 112.

As shown, methanol feed stream 201 and carbon monoxide-containing feed stream 202 are directed to liquid phase carbonylation reactor 204, in which the carbonylation reaction occurs to form acetic acid. Into carbonylation reactor 204, the methanol composition, carbon monoxide, and sufficient water are continuously introduced as needed to maintain at least a finite concentration of water, e.g., 0.1 wt. %., in the reaction medium. Gaseous purge stream 206 desirably is vented from reactor 204 to prevent buildup of gaseous by-products and to maintain a set carbon monoxide partial pressure at a given total reactor pressure. Stream 113 comprising a crude, unflashed acetic acid product exits reactor 204.

The crude acetic acid product may be purified in separation zone 208 to recover the acetic acid and recycle catalyst solution, methyl iodide, methyl acetate, and other system components within the process.

Crude product is drawn off from the carbonylation reactor 204 and is provided to flash vessel 212 via stream 213. As shown in FIG. 2, stream 213 may be directed to optional condenser 214, in which vapor that may be present is condensed. Measurement device 215 is disposed along line 213. Measurement device 215 measures the flow rate of crude acetic acid product to the flash vessel, e.g., the flash flow rate. This flash flow rate may be utilized in the disclosed control schemes to control light ends column operation and/or decanter liquid level control. Preferably, measurement device 215 is in communication with other control hardware associated with the light ends column and or the decanter (not shown). It is well within the purview of the art to select proper control hardware to implement the disclosed control schemes.

In flash vessel 212, the crude product is separated in a flash separation step to obtain a volatile ("vapor") overhead stream (a first vapor stream) 222 comprising acetic acid and a less volatile (liquid) residue stream 210 comprising a catalyst-containing solution (predominantly acetic acid containing the rhodium and the iodide salt along with lesser quantities of methyl acetate, methyl iodide, and water), which preferably is recycled to the reactor, as discussed above.

The overhead stream from flash vessel 212 is directed to the light ends column 224 as stream 222, where distillation yields a low-boiling overhead vapor stream 226, a purified acetic acid product that preferably is removed via a sidedraw 228, and a high boiling residue stream 116. Acetic acid removed via sidedraw 228 preferably is subjected to further purification, such as in drying column 230 for selective separation of acetic acid from water.

It has been disclosed in U.S. Pat. Nos. 6,143,930 and 6,339,171 that there is generally a higher concentration of the PRCs, and in particular acetaldehyde concentration, in the low-boiling overhead vapor stream exiting the light ends column than in the high-boiling residue stream exiting the column. Thus, in some cases, low-boiling overhead vapor stream 226, containing PRCs, is subjected to additional processing in PRS 232 to reduce and/or remove the amount of PRCs present. As shown, low-boiling overhead vapor stream 226, therefore, is condensed and directed to an overhead phase separation unit, as shown by overhead receiver decanter 234. In addition to PRCs, low-boiling overhead vapor stream 226 may typically contain methyl iodide, methyl acetate, acetic acid, and water.

Conditions are desirably maintained in the process such that low-boiling overhead vapor stream 226, once in decanter 234, may separate to form at least one liquid phase, e.g., a light phase and/or a heavy phase. Generally, low-boiling overhead vapor stream 226 is cooled to a temperature sufficient to condense and separate the condensable methyl iodide, methyl acetate, acetaldehyde and other carbonyl components, and water to form two phases. A portion of stream 226 may include noncondensable gases such as carbon monoxide, carbon dioxide, hydrogen, and the like that can be vented as shown by stream 236 in FIG. 2, which may be directed to a low pressure absorber unit (not shown).

The condensed light phase exits decanter 234 via line 231. The condensed heavy phase exits decanter via line 218. As shown in FIG. 2, at least a portion of the light phase and/or the heavy phase may be refluxed back to light ends column 224. A portion of the light phase in line 231 may be refluxed to light ends column 224 via line 231', thus establishing a reflux loop with line 226, decanter 234, line 231', and light ends column 224. A portion of the heavy phase in line 218 may be refluxed back to light ends column 224 via line 218'(with or without the light phase in line 231'), thus establishing a reflux loop with line 226, decanter 234, line 218', and light ends column 224. The reflux rate of streams 231' and/or 218' may be utilized to maintain light ends column operations and/or the liquid level in decanter 234.

In addition to the portions of the light phase that may be refluxed 231', a separate portion of stream 231 may be directed to PRS 232. Stream 231" directs separate portion of stream 231 to PRS 232 via line 238. In addition to the heavy phase that may be refluxed, 218', a separate portion of stream 218 may be directed to PRS 232. Stream 218" directs a separate portion of stream 218 to PRS 232 after being combined with line 231" (optionally stream 218" could be directly fed to PRS 232. In view of the control schemes discussed herein the composition of streams 218" and 231" may be more consistent, which will advantageously lead to more effective separations in PRS 232.

As shown in FIG. 2, the light phase exits decanter 234 via stream 231. A portion, e.g., aliquot portion, of light phase stream 231" is directed to PRS 232. Another portion, e.g., aliquot portion, of the light phase stream 231 optionally may be recycled to reactor 204 as shown by recycle stream 214, when additional water is desired or needed in reactor 204, although this recirculation may not necessary for process control reasons.

As indicated above, in addition to the overhead phase, light ends column 224 also forms an acetic acid sidedraw 228, which preferably comprises primarily acetic acid and water. In order to maintain an efficient product separation, it is important that the composition of sidedraw 228 does not vary or fluctuate significantly during normal operation. As previously discussed, the control schemes disclosed herein provide for improvements in the compositional consistency of sidedraw 228.

Since sidedraw 228 contains water in addition to acetic acid, sidedraw 228 from light ends column 224 preferably is directed to drying column 230, in which the acetic acid and water are separated from one another. As shown, drying column 230, separates acetic acid sidedraw 228 into overhead stream 244 comprised primarily of water and bottoms stream 246 comprised primarily of acetic acid.

Drying column bottoms stream 246 preferably comprises or consists essentially of acetic acid, with minor amounts of hydrogen iodide. In preferred embodiments, drying column bottoms stream 246 comprises acetic acid in an amount greater than 90 wt. %, e.g., greater than 95 wt. % or greater than 98 wt. %. Optionally, drying column bottoms stream 246 may be further processed, e.g., by passing through an ion exchange resin, prior to being stored or transported for commercial use.

PRC Removal System (PRS)

In some embodiments, a portion of light liquid phase and/or heavy liquid phase may be separated and directed to PRC removal system to recover methyl iodide and methyl acetate during the acetaldehyde removal process. As shown in Tables 1 and 2 above, light liquid phase and/or heavy liquid phase each contain PRC's and the process may include removing carbonyl impurities, such as acetaldehyde, that deteriorate the quality of the acetic acid product and may be removed in suitable impurity removal columns and absorbers as described in U.S. Pat. Nos. 6,143,930; 6,339, 171; 7,223,883; 7,223,886; 7,855,306; 7,884,237; 8,889, 904; and US Pub. Nos. 2006/0011462, which are incorporated herein by reference in their entirety. Carbonyl impurities, such as acetaldehyde, may react with iodide catalyst promoters to form alkyl iodides, e.g., ethyl iodide, propyl iodide, butyl iodide, pentyl iodide, hexyl iodide, etc. Also, because many impurities originate with acetaldehyde, it is desirable to remove carbonyl impurities from the liquid light phase.

The portion of light liquid phase and/or heavy liquid phase fed to the acetaldehyde or PRC removal system may vary from 1% to 99% of the mass flow of either the light liquid phase and/or heavy liquid phase, e.g., from 1 to 50%, from 2 to 45%, from 5 to 40%, 5 to 30% or 5 to 20%. Also in some embodiments, a portion of both the light liquid phase and heavy liquid phase may be fed to the acetaldehyde or PRC removal system. The portion of the light liquid phase not fed to the acetaldehyde or PRC removal system may be refluxed to the first column or recycled to the reactor, as described herein. The portion of the heavy liquid phase not fed to the acetaldehyde or PRC removal system may be recycled to the reactor. Although a portion of heavy liquid phase may be refluxed to the first column, it is more desirable to return the methyl iodide enriched heavy liquid phase to the reactor.

In some cases, it may be advantageous to remove PRCs, primarily aldehydes such as acetaldehyde, from a low-boiling overhead vapor stream of the light ends distillation column, more preferably from the condensed light phase of the low-boiling overhead vapor stream from the light ends distillation column. One or more of the streams from the PRC removal system may be returned to the system, e.g., recycled, either directly or indirectly. In some cases, no return streams from the PRC removal system are directed to the reactor or to the recycle lines to the reactor. The PRC removal system preferably includes at least one distillation column and at least one extraction column to reduce and/or remove PRC's. US Patent Publication No. 2011/0288333, which is hereby incorporated by reference, describes various PRS embodiments that may be employed with the present process.

The PRC removal system shown in FIGS. 1 and 2 may contain a single extraction step or may include multiple extraction stages, as described for example in U.S. Pat. No. 7,223,886 and optionally including multistage countercurrent extraction. According to various embodiments, one or more streams derived from either or both (i) the PRC removal system distillation column and/or (ii) the PRC removal system extraction stage, for example, may be returned to the system, e.g., either or both (i) the light ends removal column and/or (ii) the drying column of the separation system for the acetic acid production system. For example, a first portion, e.g., an aliquot portion, of a bottoms stream from a PRC removal system column may be directed to the light ends column for further processing, or a second portion, e.g., an aliquot portion, of a bottoms stream from a PRC removal system column may be directed to the drying column, preferably the upper portion of the drying column, for further processing. As another example, a raffinate from a PRS extraction unit, notably containing methyl iodide, may be returned to the system, e.g., the light ends column or the drying column or the raffinate may be added directly to the decanter and/or may be returned to the reactor.

For purposes of the present specification and claims, the overhead streams and overhead decanters of the light ends removal column and the drying column are considered to be part of the light ends removal column and of the drying column.

As indicated above, either phase of the low-boiling overhead vapor stream may be subsequently processed to remove PRCs.

For purposes of the present specification, it should be understood that the term "aliquot portion" refers to both: (i) a portion of a parent stream that has the same composition as the parent stream from which it is derived, and (ii) a stream comprising a portion of a parent stream that has the same composition as the parent stream from which it is derived and one or more additional streams that have been combined therewith. Thus, directing a return stream comprising an aliquot portion of a PRS distillation bottoms stream to the light ends column encompasses the direct transfer of a portion of the PRS distillation bottoms stream to the light ends column as well as the transfer of a derivative stream comprising (i) a portion of the PRS distillation bottoms stream and (ii) one or more additional streams that are combined therewith prior to introduction into the light ends column. An "aliquot portion" would not include, for example, streams formed in a distillation step or a phase separation step, which would not be compositionally the same as the parent stream from which they are derived nor derived from such a stream.

In addition, it has now been discovered that the use of an absorber tower that employs the (alternating) use of multiple scrubber solvents can be used to effectively separate hydrogen iodide from any of several acetic acid production process streams. Exemplary process streams that may be used as the absorber tower feed include a reactor vent stream, a flash vent stream, a light ends distillate, a PRC removal system overhead (or a vent from an accompanying receiver) and derivatives of these process streams. The specific combination of scrubbing solvents, as described herein, effectively remove hydrogen iodide from the respective process stream advantageously decreasing the corrosive effects thereof. As a result, metallurgical problems throughout the reaction and separation zones are minimized. In addition, it has been surprisingly found that the use of the specific solvents of the present invention may beneficially lead to the formation of additional methyl iodide, which can then be utilized to increase catalyst stability in the reaction zone (or elsewhere). Without being bound by theory, when methanol and/or methyl acetate are used as a scrubbing solvent, e.g., as a second scrubbing solvent, the methanol and/or methyl acetate may react with hydrogen iodide in the various acetic acid production process streams to form the additional methyl iodide. The processes of the present invention improve the purification of the crude acetic acid product by improving hydrogen iodide removal, increasing methyl iodide formation, and beneficially improving overall catalyst stability.

The distillation columns of the present invention may be a conventional distillation column, e.g., a plate column, a packed column, and others. Plate columns may include a perforated plate column, bubble-cap column, Kittel tray column, uniflux tray, or a ripple tray column. For a plate column, the theoretical number of plates is not particularly limited and depending on the species of the component to be separate, may include up to 80 plates, e.g., from 2 to 80, from 5 to 60, from 5 to 50, or more preferably from 7 to 35. The distillation column may include a combination of different distillation apparatuses. For example, a combination of bubble-cap column and perforated plate column may be used as well as a combination of perforated plate column and a packed column.

The distillation temperature and pressure in the distillation system can suitably be selected depending on the condition such as the species of the objective carboxylic acid and the species of the distillation column, or the removal target selected from the lower boiling point impurity and the higher boiling point impurity according to the composition of the feed stream. For example, in a case where the purification of acetic acid is carried out by the distillation column, the inner pressure of the distillation column (usually, the pressure of the column top) may be from 0.01 to 1 MPa, e.g., from 0.02 to 0.7 MPa, and more preferably from 0.05 to 0.5 MPa in terms of gauge pressure. Moreover, the distillation temperature for the distillation column, namely the inner temperature of the column at the temperature of the column top, can be controlled by adjusting the inner pressure of the column, and, for example, may be from 20 to 200° C., e.g., from 50 to 180° C., and more preferably from 100 to 160° C.

The material of each member or unit associated with the distillation system, including the columns, valves, condensers, receivers, pumps, reboilers, and internals, and various lines, each communicating to the distillation system may be suitable material such as glass, metal, ceramic, or combinations thereof, and is not particularly limited to a specific one. According to the present invention, the material of the foregoing distillation system and various lines are a transition metal or a transition-metal-based alloy such as iron alloy, e.g., a stainless steel, nickel or nickel alloy, zirconium or zirconium alloy thereof, titanium or titanium alloy thereof, or aluminum alloy. Suitable iron-based alloys include any alloy containing iron as a main component, e.g., a stainless steel that also comprises chromium, nickel, molybdenum and others. Suitable nickel-based alloys include any alloys containing nickel as a main component and one or more of chromium, iron, cobalt, molybdenum, tungsten, manganese, and others, e.g., HASTELLOY™ and INCONEL™. Corrosion-resistant metals may be particularly suitable as materials for the distillation system and various lines.

One of ordinary skill in the art having the benefit of this disclosure can design and operate a PRS distillation column to achieve the desired results. Accordingly, the practice of this process is not necessarily limited to specific characteristic of a particular distillation column or the operation characteristics thereof, such as the total number of stages, the feed point, reflux ratio, feed temperature, reflux temperature, column temperature profile, and the like.

As is evident from the figures and text presented above, a variety of embodiments are contemplated:

E1. A process for producing acetic acid comprising:
carbonylating at least one reactant selected from the group consisting of methanol, dimethyl ether, methyl acetate, and mixtures thereof, in the presence of a metal catalyst, methyl iodide, a halide salt, and optionally a finite amount water, to form a crude acetic acid product;
conveying the crude acetic acid product to a flash vessel at a flash flow rate;
flashing the crude acetic acid product to form a first vapor stream comprising acetic acid and methyl iodide and a first liquid residue stream comprising metal catalyst and halide salt;
separating, in a light ends column, the flashed first vapor stream to form a second vapor stream comprising methyl iodide and optionally acetaldehyde, a sidedraw comprising purified acetic acid product and optionally water, and a second liquid residue stream;
condensing, in a decanter, at least a portion of the second vapor stream to form at least one liquid phase;
refluxing to the light ends column at least a portion of the at least one liquid phase at a reflux rate;
wherein the reflux rate is adjusted based on changes in the flash flow rate.

E2. The process according to embodiment E1, further comprising the step of controlling a liquid level in the decanter based on at least one of flash flow rate and reflux rate.

E3. The process according to embodiment E2, wherein the controlling comprises measuring the flash flow rate and adjusting the reflux rate in response to the measuring E4. The process according to embodiment E2, wherein the controlling comprises decreasing the flash flow rate when the liquid level increases.

E5. The process according to embodiment E2, wherein the controlling comprises increasing the flash flow rate when the liquid level decreases E6. The process according to embodiment E2, wherein the liquid level in the decanter varies by +/−5%, under steady state operation.

E7. The process according to any one of embodiments E1 to E6, wherein the water concentration in the sidedraw varies by +/−0.3%, under steady state operation.

E8. The process according to any one of embodiments E1 to E7, wherein the water concentration in the sidedraw ranges from 1.1 wt % to 3 wt %.

E9. The process according to any one of embodiments E1 to E8, wherein the carbonylation occurs in a reactor and water content in the reactor is maintained at a substantially constant level, under steady state operation.

E10. The process according to any one of embodiments E1 to E9, wherein the at least one liquid phase comprises at least a portion of the heavy phase and the specific gravity of the heavy phase varies by +/−0.05, under steady state operation.

E11. The process according to any one of embodiments E1 to E10, wherein the at least one liquid phase comprises at least a portion of the heavy phase and the specific gravity of the heavy phase ranges from 1.5 to 1.8, under steady state operation.

E12. The process according to any one of embodiments E1 to E11, further comprising directing a second portion of the at least one liquid phase to a PRC removal system at a PRS feed rate.

E13. The process according to embodiments E12, wherein the PRS feed rate varies by +/−25%, under steady state operation.

E14. The process according to any one of embodiments E1 to E13, wherein the at least one liquid phase comprises at least a portion of the light phase and the specific gravity of the light phase varies by +/−0.05, under steady state operation.

E15. The process according to any one of embodiments E1 to E14, wherein the at least one liquid phase comprises at least a portion of the light phase and the specific gravity of the light phase ranges from 0.9 to 1.2, under steady state operation.

E16. A process for producing acetic acid comprising:
carbonylating at least one reactant selected from the group consisting of methanol, dimethyl ether, methyl acetate, and mixtures thereof, in the presence of a metal catalyst, methyl iodide, a halide salt, and optionally a finite amount water, to form a crude acetic acid product
flashing the crude acetic acid product to form a first vapor stream comprising acetic acid and methyl iodide and a first liquid residue stream comprising metal catalyst and halide salt;
separating, in a light ends column, the flashed vapor stream to form a second vapor stream comprising methyl iodide and optionally acetaldehyde, a sidedraw comprising purified acetic acid product and water, and a second liquid residue stream;
condensing, in a decanter, at least a portion of the second vapor stream to form at least one liquid phase;
refluxing to the light ends column at least a portion of the at least one liquid phase at a reflux rate;
controlling a liquid level in the decanter by adjusting or controlling the reflux rate;
wherein the water concentration in the sidedraw varies by +/−0.3%, under steady state operation.

E17. The process according to any one of embodiments E1 to E16, comprising:

carbonylating at least one reactant selected from the group consisting of methanol, dimethyl ether, methyl acetate, and mixtures thereof, in the presence of a metal catalyst, methyl iodide, a halide salt, and optionally a finite amount water, to form a crude acetic acid product flashing the crude acetic acid product to form a first vapor stream comprising acetic acid and methyl iodide and a first liquid residue stream comprising metal catalyst and halide salt;

separating, in a light ends column, the flashed vapor stream to form a second vapor stream comprising methyl iodide and optionally acetaldehyde, a sidedraw comprising purified acetic acid product and water, and a second liquid residue stream;

condensing, in a decanter, at least a portion of the second vapor stream to form at least one liquid phase;

refluxing to the light ends column at least a portion of the at least one liquid phase at a reflux rate;

controlling a liquid level in the decanter by adjusting or controlling the reflux rate;

wherein the water concentration in the sidedraw varies by +/−0.3%, under steady state operation.

E18. The process according to embodiment E17, wherein the water concentration in the sidedraw ranges from 1.1 wt % to 3 wt %.

E19. The process according to embodiment E11 or E18, wherein the liquid level in the decanter varies by +/−5%, under steady state operation.

E20. The process according to any one of embodiments E17 to E19, wherein the at least one liquid phase comprises a heavy phase and the specific gravity of the heavy phase varies by +/−0.05, under steady state operation.

E21. The process according to any one of embodiments E11 to E20, wherein the at least one liquid phase comprises a heavy phase and the specific gravity of the heavy phase ranges from 1.5 to 1.8, under steady state operation.

E22. The process according to any one of embodiments E17 to E21, wherein the at least one liquid phase comprises a light phase and the specific gravity of the light phase varies by +/−0.05, under steady state operation.

E23. The process according to any one of embodiments E17 to E22, wherein the at least one liquid phase comprises a light phase and the specific gravity of the light phase ranges from 0.9 to 1.2, under steady state operation.

E24. The process according to any one of embodiments E1 to E17, wherein the water concentration in the sidedraw ranges from 1.1 wt % to 3 wt %.

E25. The process according to any one of embodiments E1 to E18, wherein the liquid level in the decanter varies by +/−5%, under steady state operation.

E26. The process according to any one of embodiments E1 to E19, wherein the at least one liquid phase comprises a heavy phase and the specific gravity of the heavy phase varies by +/−0.05, under steady state operation.

E27. The process according to any one of embodiments E1 to E20, wherein the at least one liquid phase comprises a heavy phase and the specific gravity of the heavy phase ranges from 1.5 to 1.8, under steady state operation.

E28. The process according to any one of embodiments E1 to E21, wherein the at least one liquid phase comprises a light phase and the specific gravity of the light phase varies by +/−0.05, under steady state operation.

E29. The process according to any one of embodiments E1 to E22, wherein the at least one liquid phase comprises a light phase and the specific gravity of the light phase ranges from 0.9 to 1.2, under steady state operation.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing acetic acid, the process comprising:

carbonylating at least one reactant selected from the group consisting of methanol, dimethyl ether, methyl acetate, and mixtures thereof, in the presence of a metal catalyst, methyl iodide, a halide salt, and optionally a finite amount water, to form a crude acetic acid product;

conveying the crude acetic acid product to a flash vessel at a flash flow rate and measuring the flash flow rate;

flashing the crude acetic acid product to form a first vapor stream comprising at least some of the acetic acid and at least some of the methyl iodide and a first liquid residue stream comprising at least some of the metal catalyst and at least some of the halide salt;

separating, in a light ends column, the flashed first vapor stream to form a second vapor stream comprising at least some of the methyl iodide and optionally acetaldehyde, a sidedraw comprising purified acetic acid product and optionally water, and a second liquid residue stream;

condensing, in a decanter, at least a portion of the second vapor stream to form a heavy phase and a light phase;

refluxing to the light ends column at least a portion of at least one phase selected from the group consisting of the heavy phase and the light phase at a reflux rate; and adjusting the reflux rate based on the measured flash flow rate.

2. The process of claim 1, further comprising the step of controlling a liquid level in the decanter based on at least one of flash flow rate and reflux rate.

3. The process of claim 2, wherein the controlling comprises decreasing the flash flow rate when the liquid level increases.

4. The process of claim 2, wherein the controlling comprises increasing the flash flow rate when the liquid level decreases.

5. The process of claim 2, wherein the liquid level in the decanter varies by +/−5%, under steady state operation.

6. The process of claim 1, wherein the water concentration in the sidedraw varies by +/−0.3%, under steady state operation.

7. The process of claim 1, wherein the water concentration in the sidedraw ranges from 1.1 wt % to 3 wt %.

8. The process of claim 1, wherein the carbonylation occurs in a reactor and water content in the reactor is maintained at a substantially constant level, under steady state operation.

9. The process of claim 1, wherein the at least one liquid phase comprises at least a portion of the heavy phase and the specific gravity of the heavy phase varies by +/−0.05, under steady state operation.

10. The process of claim 1, wherein the at least one liquid phase comprises at least a portion of the heavy phase and the specific gravity of the heavy phase ranges from 1.5 to 1.8, under steady state operation.

11. The process of claim 1, further comprising directing a second portion of the at least one liquid phase to a PRC removal system at a PRS feed rate.

12. The process of claim 11, wherein the PRS feed rate varies by +/−25%, under steady state operation.

13. The process of claim 1, wherein the at least one liquid phase comprises at least a portion of the light phase and the specific gravity of the light phase varies by +/−0.05, under steady state operation.

14. The process of claim 1, wherein the at least one liquid phase comprises at least a portion of the light phase and the specific gravity of the light phase ranges from 0.9 to 1.2, under steady state operation.

15. A process for producing acetic acid, the process comprising:
 carbonylating at least one reactant selected from the group consisting of methanol, dimethyl ether, methyl acetate, and mixtures thereof, in the presence of a metal catalyst, methyl iodide, a halide salt, and optionally a finite amount water, to form a crude acetic acid product;
 conveying the crude acetic acid product to a flash vessel at a flash flow rate and measuring the flash flow rate;
 flashing the crude acetic acid product to form a first vapor stream comprising at least some of the acetic acid and at least some of the methyl iodide and a first liquid residue stream comprising at least some of the metal catalyst and at least some of the halide salt;
 separating, in a light ends column, the flashed vapor stream to form a second vapor stream comprising at least some of the methyl iodide and optionally acetaldehyde, a sidedraw comprising purified acetic acid product and water, and a second liquid residue stream;
 condensing, in a decanter, at least a portion of the second vapor stream to form a heavy phase and a light phase;
 refluxing to the light ends column at least a portion of at least one phase selected from the group consisting of the heavy phase and the light phase at a reflux rate; and
 controlling a liquid level in the decanter by adjusting or controlling the reflux rate based on the measured flash flow rate.

16. The process of claim 15, wherein the water concentration in the sidedraw ranges from 1.1 wt % to 3 wt %.

17. The process of claim 15, wherein the liquid level in the decanter varies by +/−5%, under steady state operation.

18. The process of claim 15, wherein the at least one liquid phase comprises a heavy phase and the specific gravity of the heavy phase varies by +/−0.05, under steady state operation.

19. The process of claim 15, wherein the at least one liquid phase comprises a heavy phase and the specific gravity of the heavy phase ranges from 1.5 to 1.8, under steady state operation.

20. The process of claim 15, wherein the at least one liquid phase comprises a light phase and the specific gravity of the light phase varies by +/−0.05, under steady state operation.

21. The process of claim 15, wherein the at least one liquid phase comprises a light phase and the specific gravity of the light phase ranges from 0.9 to 1.2, under steady state operation.

22. The process of claim 15, further comprising the step of measuring the flash flow rate, and wherein the reflux rate is adjusted based on changes in the measured flash flow rate.

23. The process of claim 15, wherein the water concentration in the sidedraw varies by +/−0.3%, under steady state operation.

* * * * *